United States Patent [19]

Pieper et al.

[11] Patent Number: 5,442,064
[45] Date of Patent: Aug. 15, 1995

[54] CARBOXYLIC ACID DERIVATIVES, PHARMACEUTICAL COMPOSITIONS CONTAINING THESE COMPOUNDS AND PROCESSES FOR PREPARING THEM

[75] Inventors: Helmut Pieper, Biberach; Günter Linz; Frank Himmelsbach, both of Mittelbiberach; Volkhard Austel, Biberach; Thomas Müller, Biberach; Johannes Weisenberger, Biberach; Brian Guth, Warthausen, all of Germany

[73] Assignee: Dr. Karl Thomae GmbH, Biberach an der Riss, Germany

[21] Appl. No.: 135,041

[22] Filed: Oct. 12, 1993

[30] Foreign Application Priority Data

Oct. 12, 1992 [DE] Germany .................. 42 34 295.3

[51] Int. Cl.⁶ .................. C07D 401/00; C07D 295/00; C07D 211/30; C07D 211/06
[52] U.S. Cl. .................. 544/360; 544/390; 546/226; 546/189
[58] Field of Search .................. 544/360; 514/252

[56] References Cited

U.S. PATENT DOCUMENTS 5,084,466  1/1992  Alig et al. .................. 514/353
5,256,812 10/1993  Alig et al. .................. 560/35

FOREIGN PATENT DOCUMENTS 0381033  8/1990  European Pat. Off. .
0496378  7/1992  European Pat. Off. .
0518819 12/1992  European Pat. Off. .
0528369  2/1993  European Pat. Off. .
0537980  4/1993  European Pat. Off. .

OTHER PUBLICATIONS

"Low Molecular Weight, Non–Peptide Fibrinogen Receptor Antagonists"—L. Alig, et al., Journal of Medicinal Chemistry, vol. 35, No. 23, Nov. 1992; pp. 4393–4407.

Primary Examiner—Cecilia Tsang
Attorney, Agent, or Firm—R. P. Raymond; M-E. M. Devlin; A. R. Stempel

[57] ABSTRACT

The invention relates to carboxylic acid derivatives of general formula $$A-B-C-D-E-F-G \qquad (I)$$

wherein

A to G are defined as in claim 1, the tautomers thereof, the stereoisomers thereof including the mixtures thereof and the addition salts thereof, particularly the physiologically acceptable salts with inorganic or organic acids or bases, which have valuable pharmacological properties, preferably inhibitory effects on aggregation, and to pharmaceutical compositions containing the compounds and processes for preparing them.

6 Claims, No Drawings

CARBOXYLIC ACID DERIVATIVES, PHARMACEUTICAL COMPOSITIONS CONTAINING THESE COMPOUNDS AND PROCESSES FOR PREPARING THEM

The invention relates to carboxylic acid derivatives of the general formula $$A-B-C-D-E-F-G \quad (I)$$

the tautomers thereof, the stereoisomers, including mixtures thereof, and the addition salts thereof, in particular the physiologically acceptable addition salts with inorganic or organic acids or bases, which have valuable pharmacological properties, preferably aggregation-inhibiting properties, pharmaceutical compositions containing these compounds and their use as well as processes for preparing them.

In general formula I above

A denotes a straight-chained or branched aminoalkyl group, an amino, amidino or guanidino group, in which at one of the nitrogen atoms in each of the above-mentioned groups one or two hydrogen atoms may be replaced by an alkyl or phenylalkyl group or a hydrogen atom may be replaced by an alkoxycarbonyl group having a total of 2 to 5 carbon atoms, by an $R_1$—CO—O—($R_2$CH)—O—CO—, benzyloxycarbonyl or allyloxycarbonyl group, wherein $R_1$ denotes a $C_{1-5}$-alkyl group, a $C_{5-7}$-cycloalkyl group or a phenyl or phenylalkyl group and $R_2$ denotes a hydrogen atom, a $C_{1-4}$-alkyl group, a $C_{5-7}$-cycloalkyl group or a phenyl group, B denotes a 6-membered aromatic group which may contain one or two nitrogen atoms and may additionally be monosubstituted in the carbon skeleton by a trifluoromethyl group or mono- or disubstituted in the carbon skeleton by fluorine, chlorine or bromine atoms or by alkyl groups, wherein the substituents may be identical or different, C denotes a 1,4-cyclohexylene group in which a CH unit in the 1- or 4-position may be replaced by a nitrogen atom or the CH units in the 1- and 4-positions may each be replaced by a nitrogen atom, or C may denote a 1,4-cyclohexylene group wherein the methylene group in the 2-position or the methylene groups in the 2- and 5-positions are each replaced by an $NR_3$ group, whilst in a ring thus obtained which contains one or two nitrogen atoms or one or two $NR_3$ groups, a methylene group adjacent to a nitrogen atom may be replaced by a carbonyl group, or C may represent a 3,4-dehydro-1,4-piperidinylene group, wherein $R_3$ denotes a hydrogen atom or an alkyl or phenylalkyl group, D denotes a methylene, ethylene, carbonyl or methylenecarbonyl group, in which the carbonyl group of the methylenecarbonyl group is linked to the group E, or D denotes an —$NR_3$—CO—X— group in which the nitrogen atom of the —$NR_3$—CO—X— group is linked to the group C, $R_3$ is as hereinbefore defined and X denotes a straight-chained or branched $C_{1-5}$-alkylene group or a 1,4-cyclohexylene group, E denotes a 1,4-cyclohexylene or 1,4-cyclohex-3-enylene group in which the CH unit in the 1-position, which is linked to the group D, is replaced by a nitrogen atom and additionally the CH unit in a 1,4-cyclohexylene group in the 4-position, which is linked to the group F or G, may be replaced by a nitrogen atom by a >C=CH— group, or E may denote an —$NR_4$—X— group wherein X is as hereinbefore defined and $R_4$ denotes a hydrogen atom, a $C_{1-6}$-alkyl group which may be substituted in the 1-, 2- or 3-position by a morpholinocarbonyl, pyrrolidinocarbonyl, piperidinocarbonyl or hexamethyleneiminocarbonyl group or by an ($R_1NR_2$)—CO— group, wherein $R_1$ and $R_2$ are as hereinbefore defined, or $R_4$ may denote a phenylalkyl group having 1 to 4 carbon atoms in the alkyl moiety, F denotes an alkylene group or, if E does not represent a 1,4-piperazinylene group, F may also denote a bond and G denotes a carbonyl group substituted by an $R_5O$— group, wherein $R_5$ denotes a hydrogen atom, a $C_{1-6}$-alkyl group which may be substituted in the 1-, 2- or 3-position by a morpholinocarbonyl, pyrrolidinocarbonyl, piperidinocarbonyl, hexamethyleneiminocarbonyl or ($R_1NR_2$)—CO— group or may be substituted in the 2- or 3-position by a morpholino or pyrrolidinon-1-yl group, wherein $R_1$ and $R_2$ are as hereinbefore defined, or $R_5$ may denote a phenylalkyl or pyridylalkyl group, a $C_{4-8}$-cycloalkyl group or a cycloalkylalkyl group having 3 to 8 carbon atoms in the cycloalkyl moiety, wherein the cycloalkyl group in each case may be substituted by a $C_{1-4}$-alkyl group or by a $C_{1-4}$-alkyl group and by 1 to 3 methyl groups, or $R_5$ may also represent a bicycloalkyl or bicycloalkylalkyl group wherein the bicycloalkyl moiety contains 6 to 10 carbon atoms and may additionally be substituted by 1 to 3 methyl groups, or G denotes a phosphono, O-alkylphosphono, tetrazol-5-yl or $R_6CO$—O—$CHR_2$—O—CO— group, wherein $R_2$ is as hereinbefore defined and $R_6$ denotes a $C_{1-5}$-alkyl group, a cycloalkyl or cycloalkoxy group having 5 to 7 carbon atoms in the cycloalkyl moiety, a $C_{1-4}$-alkoxy group or a phenyl, phenylalkyl or phenylalkoxy group, wherein, unless otherwise specified the above-mentioned alkyl, alkylene or alkoxy moieties may each contain 1 to 3 carbon atoms.

However, preferred compounds of general formula I above are those wherein

A denotes a $C_{1-2}$-aminoalkyl group or an amidino group, in which at a nitrogen atom in the above-mentioned groups, a hydrogen atom may be replaced by an alkoxycarbonyl group having a total of 2 or 3 carbon atoms or by a benzyloxycarbonyl, allyloxycarbonyl or $R_1$—CO—O—($R_2$CH)—O—CO— group, wherein $R_1$ denotes a $C_{1-2}$-alkyl group and $R_2$ denotes a hydrogen atom or a $C_{1-2}$-alkyl group, B denotes a 6-membered aromatic group which may contain one or two nitrogen atoms and may additionally be substituted in the carbon skeleton by a fluorine, chlorine or bromine atom or by a methyl group, C denotes a 3,4-dehydro-1,4-piperidinylene group or a 1,4-cyclohexylene group in which a CH unit in the 1- or 4-position may be replaced by a nitrogen atom or the CH units in the 1- and 4-positions may each be replaced by a nitrogen atom, or C may denote a 2-oxo-1,4-piperidinylene group, D denotes a methylene, ethylene, carbonyl or methylenecarbonyl group, wherein the carbonyl group of the methylenecarbonyl group is linked to the group E, or D denotes an —$NR_3$—CO—X— group wherein the nitrogen atom of the —$NR_3$—CO—X— group is linked to the group C, $R_3$ denotes a hydrogen atom or an alkyl or phenylalkyl group having 1 to 3 carbon atoms in the alkyl moiety and X denotes a straight-chained or branched $C_{1-4}$-alkylene group or a 1,4-cyclohexylene group, E denotes a 1,4-cyclohexylene or 1,4-cyclohex-3-enylene group in which the CH unit in the 1-position, which is linked to the group D, is replaced by a nitrogen atom and additionally the CH unit in a 1,4-cyclohexylene group in the 4-position, which is linked to the group F or G, may be replaced by a nitrogen atom or by a >C=CH-group, or E may denote an —$NR_4$—X— group, wherein X is as hereinbefore defined and $R_4$ denotes a hydrogen atom, a $C_{1-6}$-alkyl group, a phenylalkyl group having 1 to 4 carbon atoms in the alkyl moiety or a morpholinocarbonylmethyl group, F denotes a methylene group or, if E does not denote a 1,4-piperazinylene group, F may also denote a bond and G denotes a carbonyl group substituted by an $R_5O$— group, wherein $R_5$ denotes a hydrogen atom, a $C_{1-6}$-alkyl group which may be substituted in the 1-position by a morpholinocarbonyl, piperidinocarbonyl or dimethylaminocarbonyl group and in the 2-position by a morpholino or pyrrolidinon-1-yl group, or $R_5$ denotes a phenylmethyl or pyridylmethyl group, a cycloalkyl or cycloalkylmethyl group each having 5 or 6 carbon atoms in the cycloalkyl moiety, or a menthyl or norbornyl group, or G denotes an $R_6CO$—O—$CHR_2$—O—CO— group wherein $R_2$ is as hereinbefore defined and $R_6$ denotes a $C_{1-4}$-alkyl group or a methoxy or ethoxy group, the tautomers thereof, the stereoisomers thereof including the mixtures thereof and the addition salts thereof.

Particularly preferred compounds of general formula I, however, are those wherein A denotes an aminomethyl or amidino group, in which at a nitrogen atom in the amidino group, a hydrogen atom may be replaced by a methoxycarbonyl, ethoxycarbonyl or benzyloxycarbonyl group, B denotes a phenylene group optionally substituted by a bromine atom, or a pyridinylene group, C denotes a 1,4-cyclohexylene group wherein a CH unit in the 1- or 4-position may be replaced by a nitrogen atom or the CH units in the 1- and 4-position may each be replaced by a nitrogen atom, D denotes a methylene, ethylene, carbonyl or methylenecarbonyl group, wherein the carbonyl group of the methylenecarbonyl group is linked to the group E, or D denotes an —$NR_3$—CO—X— group, wherein the nitrogen atom of the —$NR_3$—CO—X— group is linked to the group C, $R_3$ denotes a hydrogen atom or a $C_{1-3}$-alkyl group and X denotes a straight-chained or branched $C_{2-3}$-alkylene group or a 1,4-cyclohexylene group, E denotes a 1,4-cyclohexylene or 1,4-cyclohex-3-enylene group wherein the CH unit in the 1-position, which is linked to the group D, is replaced by a nitrogen atom and additionally the CH unit in a 1,4-cyclohexylene group in the 4-position, which is linked to the group F or G, may be replaced by a >C=CH— group, or E denotes an —$NR_4$—X— group wherein X is as hereinbefore defined and $R_4$ denotes a hydrogen atom, a $C_{1-5}$-alkyl group or a phenylalkyl group having 1 to 3 carbon atoms in the alkyl moiety, F denotes a bond or a methylene group and G denotes a carbonyl group substituted by an $R_5O$— group, wherein $R_5$ denotes a hydrogen atom, a $C_{1-5}$-alkyl group which may be substituted in the 1-position by a morpholinocarbonyl, piperidinocarbonyl or dimethylaminocarbonyl group, or $R_5$ denotes a $C_{5-6}$-cycloalkyl group, the tautomers thereof, stereoisomers thereof including mixtures thereof, and the addition salts thereof.

However, especially particularly preferred compounds of general formula I are those wherein A and B together denote a 4-aminomethyl-phenyl group, a 4-amidino-phenyl group, in which at a nitrogen atom in the amidino group, a hydrogen atom may be replaced by a methoxycarbonyl or benzyloxycarbonyl group, or a 5-amidino-pyrid-2-yl group, C denotes a 1,4-cyclohexylene group wherein a CH unit in the 1- or 4-position is replaced by a nitrogen atom or the CH units in the 1- and 4-positions are each replaced by a nitrogen atom, D denotes a methylene, ethylene, carbonyl or methylenecarbonyl group, wherein the carbonyl group of the methylenecarbonyl group is linked to the group E, or D denotes an —$NR_3$—CO—X— group in which the nitrogen atom of the —$NR_3$—CO—X— group is linked to the group C, $R_3$ denotes a hydrogen atom or a methyl group and X denotes a straight-chained or branched $C_{2-3}$-alkylene group or a 1,4-cyclohexylene group, E denotes a 1,4-cyclohexylene or 1,4-cyclohex-3-enylene group in which the CH unit in the 1-position, which is linked to the group D, is replaced by a nitrogen atom and additionally the CH unit in a 1,4-cyclohexylene group in the 4-position, which is linked to the group F or G, may be replaced by a >C=CH— group, or E may represent an —$NR_4$—X— group wherein X is as hereinbefore defined and $R_4$ denotes a hydrogen atom, a straight-chained $C_{1-5}$-alkyl group, a benzyl, 2-phenylethyl or 3-phenylpropyl group, F denotes a bond or a methylene group and G denotes a carbonyl group substituted by an $R_5$ O— group, wherein $R_5$ denotes a hydrogen atom, a $C_{1-4}$-alkyl group, a methyl group substituted by a morpholinocarbonyl or dimethylaminocarbonyl group, or $R_5$ may denote a cyclohexyl group, the stereoisomers thereof including mixtures thereof and the addition salts thereof, but particularly the compounds (a) 1-(4-amidinophenyl)-4-[N-(trans-4-carboxycyclohexyl)-aminocarbonyl]-piperazine, (b) 1-(4-amidinophenyl)-4-[N-(trans-4-carboxycyclohexyl)-N-methyl-aminocarbonyl]-piperazine, (c) 1-(5-amidinopyrid-2-yl)-4-[N-(trans-4-carboxycyclohexyl)-aminocarbonyl]-piperazine, (d) 4-(4-amidinophenyl)-1-[N-(trans-4-carboxycyclohexyl)-aminocarbonyl]-piperidine, (e) 1-(4-amidinophenyl)-4-[N-benzyl-N-(trans-4-carboxycyclohexyl)-aminocarbonyl]-piperazine, (f) 1-(5-amidinopyrid-2-yl)-4-[N-(trans-4-carboxycyclohexyl)-aminocarbonyl]-piperazine, (g) 1-(5-amidinopyrid-2-yl)-4-[N-(trans-4-carboxycyclohexyl)-N-methyl-aminocarbonyl]-piperazine, (h) 4- (4-aminomethylphenyl) -1- [N- (trans-4-carboxycyclohexyl) -aminocarbonyl]-piperidine, (i) 4-(4-amidinophenyl)-4-[4-(carboxymethyl)-piperidinocarbonyl]-piperazine, (j) 1-(4-amidinophenyl)-4-[4-(carboxymethyl)-3,4-dehydro-piperidinocarbonyl]-piperazine, (k) 1-(5-aminomethylpyrid-2-yl) -4-[N-(trans-4-carboxycyclohexyl)-aminocarbonyl]-piperazine, (l) 1-(5-amidinopyrid-2-yl )-4-[4-(carboxymethyl) -piperidinocarbonyl]-piperidine, (m) 1-(4-aminomethylphenyl)-4-[N-(trans-4-carboxycyclohexyl)-aminocarbonyl]-piperazine, (n) 1-[4-(N-benzyloxycarbonyl-amidino)-phenyl]-4-[N-(trans-4-carboxycyclohexyl)-aminocarbonyl]-piperazine, (o) 4-(4-amidinophenyl)-1-[N-(trans-4-carboxycyclohexyl)-aminocarbonyl]-piperidine, (p) 1-(4-amidinophenyl)-4-[4-(carboxymethyl)-piperidinocarbonyl]-piperidine, (q) 1-(4-amidinophenyl)-4-[N-(2-carboxyethyl)-aminocarbonylmethyl]-piperidine, (r) 1-(4-amidinophenyl) -4-[N-(trans-4-carboxycyclohexyl) -aminocarbonyl]-piperidine, (s) 1-(4-aminomethylphenyl)-4-[N-(trans-4-carboxycyclohexyl)-aminocarbonyl]-piperidine, (t) 1-(4-amidinophenyl)-4-[N-(trans-4-carboxycyclohexyl)-N-(2-phenylethyl)-aminocarbonyl]-piperidine, (u) 1-(4-amidinophenyl)-4-[N-(trans-4-carboxycyclohexyl)-N-(3-phenylpropyl)-aminocarbonyl]-piperidine and (v) 1-(4-amidinophenyl)-4-[N-(trans-4-carboxycyclohexyl)-N-(n-pentyl)-aminocarbonyl]-piperidine, the esters thereof with cyclohexanol or with a $C_{1-4}$-alkanol, wherein methanol may be substituted by a morpholinocarbonyl or dimethylaminocarbonyl group, the stereoisomers thereof, including mixtures thereof and the addition salts thereof.

According to the invention, the new compounds of general formula I may, for example, be prepared using the following methods:

a) In order to prepare compounds of general formula I wherein G denotes a carboxyl group:
Conversion of a compound of general formula

$$A—B—C—D—E—F—G'\quad\quad(II)$$

wherein
A, B, C, D, E and F are as hereinbefore defined and G', which is bound to a carbon atom, denotes a group which can be converted into a carboxyl group by hydrolysis, treatment with acids, thermolysis or hydrogenolysis.

For example, functional derivatives of the carboxyl group such as unsubstituted or substituted amides, Esters, thioesters, trimethylsilylesters, orthoesters, iminoesters, amidines or anhydrides, or a nitrile group may be converted by hydrolysis into a carboxyl group, esters with tertiary alcohols, e.g. tert.butylesters, may be converted by treatment with an acid or thermolysis into a carboxyl group, and esters with aralkanols, e.g. benzylesters, may be converted by hydrogenolysis into a carboxyl group, and bis(alkoxycarbonyl)methyl groups may be converted by hydrolysis or treatment with an acid into a bis(hydroxycarbonyl)methyl group, which is subsequently decarboxylated.

The hydrolysis is appropriately carried out either in the presence of an acid such as hydrochloric acid, sulphuric acid, phosphoric acid, trichloroacetic acid or trifluoroacetic acid, in the presence of a base such as lithium hydroxide, sodium hydroxide or potassium hydroxide in a suitable solvent such as water, methanol, water/methanol, ethanol, water/ethanol, water/isopropanol, water/tetrahydrofuran or water/dioxane at temperatures between $-10°$ C. and 120° C., e.g. at temperatures between ambient temperature and the boiling temperature of the reaction mixture. When treating with an organic acid such as trichloroacetic acid or trifluoroacetic acid, any alcoholic hydroxy groups present may simultaneously be converted into a corresponding acyloxy group such as a trifluoroacetoxy group.

When G' in a compound of formula II represents a cyano or aminocarbonyl group, these groups may also be converted into a carboxyl group with a nitrite, e.g. sodium nitrite, in the presence of an acid such as sulphuric acid, which at the same time may appropriately be used as the solvent, at temperatures between 0° and 50° C.

When G' in a compound of formula II represents, for example, a tert.butyloxycarbonyl group, the tert.butyl group may also be cleaved by treating with an acid such as trifluoroacetic acid, hydrochloric acid, formic acid, p-toluenesulphonic acid, sulphuric acid, phosphoric acid or polyphosphoric acid, optionally in an inert solvent such as methylene chloride, chloroform, benzene, toluene, tetrahydrofuran or dioxane, preferably at temperatures between $-10°$ C. and 120° C., e.g. at temperatures between 0° and 66° C., or thermally, optionally in an inert solvent such as methylene chloride, chloroform, benzene, toluene, tetrahydrofuran or dioxane and optionally in the presence of a catalytic amount of an acid such as p-toluenesulphonic acid, sulphuric acid, phosphoric acid or polyphosphoric acid, preferably at the boiling temperature of the solvent used, e.g. at temperatures between 40° C. and 100° C.

When G' in a compound of formula II represents, for example, a benzyloxycarbonyl group, the benzyl group may also be hydrogenolytically cleaved in the presence of a hydrogenation catalyst such as palladium/charcoal in a suitable solvent such as methanol, ethanol, ethanol/water, glacial acetic acid, ethyl acetate, dioxane or dimethylformamide, preferably at temperatures between 0° and 50° C., e.g. at ambient temperature, under a hydrogen pressure of 1 to 10 bar. During hydrogenolysis, other groups may also be reduced at the same time, e.g. a nitro group may be reduced to an amino group or a benzyloxy group to a hydroxy group, or a benzyloxycarbonylamidino group into an amidino group.

b) In order to prepare compounds of general formula I wherein A denotes an amidino group in which, at one of the nitrogen atoms, one or two hydrogen atoms may be replaced by an alkyl or phenylalkyl group:
Reacting a compound of general formula

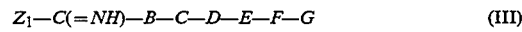
$$Z_1—C(=NH)—B—C—D—E—F—G\quad\quad(III)$$

optionally formed in the reaction mixture, wherein B, C, D, E, F and G are as hereinbefore defined and $Z_1$ denotes an alkoxy or aralkoxy group such as a methoxy, ethoxy, n-propoxy, isopropoxy or benzyloxy group or an alkylthio or aralkylthio group such as a methylthio, ethylthio, n-propylthio or benzylthio group or an amino group, with an amine of general formula $$R_a\text{---}NH\text{---}R_b \qquad (IV)$$

wherein $R_a$ and $R_b$, which may be identical or different, represent hydrogen atoms or alkyl or phenylalkyl groups each having 1 to 3 carbon atoms in the alkyl moiety.

The reaction is expediently carried out in a solvent such as methanol, ethanol, n-propanol, water, methanol/water, tetrahydrofuran or dioxane at temperatures between 0° and 150° C., preferably at temperatures between 20° and 120° C., with a corresponding free amine or with a corresponding acid addition salt such as, for example, ammonium carbonate or ammonium acetate.

A compound of general formula III may be obtained, for example, by reacting a corresponding nitrile with a suitable alcohol such as methanol, ethanol, n-propanol, isopropanol or benzyl alcohol in the presence of an acid such as hydrochloric acid or in the presence of a corresponding alkoxide such as sodium methoxide or ethoxide or by reacting a corresponding amide with a trialkyloxonium salt such as triethyloxonium-tetrafluoroborate in a solvent such as methylene chloride, tetrahydrofuran or dioxane at temperatures between $-10°$ and 50° C., but preferably between 0° and 20° C., or a corresponding nitrile with hydrogen sulphide, appropriately in a solvent such as pyridine or dimethylformamide and in the presence of a base such as triethylamine with subsequent alkylation of the resulting thioamide with a corresponding alkyl or aralkyl halide.

c) In order to prepare compounds of general formula I wherein A denotes an amidino group:
Reaction of a compound of general formula $$NC\text{---}B\text{---}C\text{---}D\text{---}E\text{---}F\text{---}G \qquad (v)$$

wherein

B, C, D, E, F and G are as hereinbefore defined, with hydroxylamine followed by reduction of the amidoxime thus obtained.

The reaction with hydroxylamine is appropriately carried out in a solvent such as methanol, ethanol, n-propanol, water, methanol/water, ethanol/water, tetrahydrofuran or dioxane, optionally with the addition of a base such as sodium carbonate at temperatures between 0° and 100° C., but preferably at temperatures between 20° and 80° C., either with free hydroxylamine or with a corresponding acid addition salt such as the hydrochloride.

The subsequent reduction is preferably carried out in a suitable solvent such as methanol, methanol/water, methanol/ammonia, methanol/water/ammonia, methanol/hydrochloric acid, ethanol, ether, tetrahydrofuran, dioxane, dimethylformamide or glacial acetic acid in the presence of catalytically activated hydrogen, e.g. hydrogen in the presence of Raney nickel, platinum or palladium/charcoal at temperatures between 0° and 100° C., preferably at temperatures between 20° and 80° C.

d) In order to prepare compounds of general formula I wherein A denotes an amidino group in which, at one of the nitrogen atoms, one or two hydrogen atoms may be replaced by an alkyl or phenylalkyl group:
Reacting a compound of general formula $$NC\text{---}B\text{---}C\text{---}D\text{---}E\text{---}F\text{---}G \qquad (v)$$

wherein

B, C, D, E, F and G are as hereinbefore defined, with a corresponding alkylchloroaluminium amide.

The reaction is preferably carried out in a suitable solvent, e.g. in benzene or toluene, at temperatures between 0° and 100° C., but preferably at a temperature between 20° and 80° C. and the aluminium complex thus obtained is then decomposed by hydrolysis, preferably using a suspension of silica gel in chloroform (see R. S. Garigipati, Tetrahedron Letters 31, 1969 (1990)).

e) In order to prepare compounds of general formula I wherein A represents a straight-chained or branched $C_{1-3}$-aminoalkyl group:
Reduction of a compound of general formula $$A_1\text{---}B\text{---}C\text{---}D\text{---}E\text{---}F\text{---}G \qquad (VI)$$

wherein

B, C, D, E, F and G are as hereinbefore defined and $A_1$ denotes a cyano, cyanomethyl, 1-cyanoethyl or 2-cyanoethyl group.

The reduction is preferably carried out in a suitable solvent such as methanol, methanol/water, methanol/ammonia, methanol/water/ammonia, methanol/hydrochloric acid, methanol/ethereal hydrochloric acid, ethanol, ether, tetrahydrofuran, dioxane, dimethylformamide or glacial acetic acid in the presence of catalytically activated hydrogen, e.g. hydrogen in the presence of Raney nickel, platinum or palladium/charcoal, or in the presence of a metal hydride such as sodium borohydride or lithium borohydride at temperatures between 0° and 100° C., preferably at temperatures between 20° and 80° C.

f) In order to prepare compounds of general formula I wherein A is a straight-chained or branched $C_{1-3}$-aminoalkyl group or an amino, amidino or guanidino group, in which at one of the nitrogen atoms in each of the above-mentioned groups, a hydrogen atom is replaced by an alkoxycarbonyl group having a total of 2 to 5 carbon atoms, or by a benzyloxycarbonyl, allyloxycarbonyl or $R_1\text{---}CO\text{---}O\text{---}(R_2CH)\text{---}O\text{---}CO\text{---}$ group, wherein $R_1$ and $R_2$ are as hereinbefore defined:
Reacting a compound of general formula $$A_2\text{---}B\text{---}C\text{---}D\text{---}E\text{---}F\text{---}G \qquad (VII)$$

wherein

B, C, D, E, F and G are as hereinbefore defined and $A_2$ denotes a straight-chained or branched $C_{1-3}$-aminoalkyl group or an amino, amidino or guanidino group, with a compound of general formula $$Z_2\text{---}R_c \qquad (VIII)$$

wherein $R_c$ denotes an alkoxycarbonyl group having a total of 2 to 5 carbon atoms, a benzyloxycarbonyl, allyloxycarbonyl or $R_1\text{---}CO\text{---}O\text{---}(R_2CH)\text{---}O\text{---}CO\text{---}$ group, wherein $R_1$ and $R_2$ are as hereinbefore defined, and $Z_2$ denotes a nucleophilic leaving group such as a halogen atom, e.g. a chlorine or bromine atom, or an optionally substituted phenoxy group, e.g. a p-nitrophenoxy group.

The reaction is conveniently carried out in a solvent or mixture of solvents such as water, tetrahydrofuran, tetrahydrofuran/water, dioxane, dioxane/water, methylene chloride, chloroform, ethyl acetate or dimethylformamide, appropriately in the presence of a base such as sodium carbonate, potassium carbonate or sodium hydroxide solution or in the presence of a tertiary organic base such as triethylamine, N-ethyl-diisopropylamine, N-methyl-morpholine or pyridine, which may simultaneously serve as solvent, at temperatures between $-30°$ and $100°$ C., but preferably at temperatures between $-10°$ and $80°$ C.

g) In order to prepare compounds of general formula I wherein G denotes a carbonyl group substituted by an $R_5'O-$ group, wherein $R_5'$ has the meanings given for $R_5$ hereinbefore, with the exception of the hydrogen atom:

Reacting a compound of general formula

  (IX)

wherein

A, B, C, D, E and F are as hereinbefore defined and $G_1$ denotes a carboxy or alkoxycarbonyl group, with an alcohol of general formula $$HO-R_5' \quad (X)$$

wherein $R_5'$ has the meanings given for $R_5$ hereinbefore, with the exception of the hydrogen atom.

The reaction is conveniently carried out in a solvent or mixture of solvents such as methylene chloride, dimethylformamide, dimethylsulphoxide, benzene, toluene, chlorobenzene, tetrahydrofuran, benzene/tetrahydrofuran or dioxane, optionally in the presence of an acid such as hydrochloric acid or in the presence of a dehydrating agent, e.g. in the presence of isobutylchloroformate, thionylchloride, trimethylchlorosilane, hydrochloric acid, sulphuric acid, methanesulphonic acid, p-toluenesulphonic acid, phosphorustrichloride, phosphoruspentoxide, N,N'-dicyclohexylcarbodiimide, N,N'-dicyclohexylcarbodiimide/N-hydroxysuccinimide, dimethylaminopyridine or 1-hydroxybenzotriazole, N,N'-carbonyldiimidazole or N,N'-thionyldiimidazole or triphenylphosphine/carbon tetrachloride, expediently at temperatures between $0°$ and $150°$ C., preferably at temperatures between $0°$ and $50°$ C.

The reaction of a corresponding alkoxy compound of general formula IX with an alcohol of general formula X is preferably carried out in the alcohol in question as solvent, optionally in the presence of another solvent such as methylene chloride or ether, preferably in the presence of an acid such as hydrochloric acid at temperatures between $0°$ and $100°$ C., preferably at temperatures between 20 and $80°$ C.

h) In order to prepare compounds of general formula I wherein G denotes a carbonyl group substituted by an $R_5'O-$ group, or an $R_6CO-O-CHR_2-O-CO-$ group, wherein $R_2$ and $R_6$ are as hereinbefore defined and $R_5'$ has the meanings given for $R_5$ hereinbefore, with the exception of the hydrogen atom:

Reacting a compound of general formula

  (XI)

wherein

A, B, C, D, E and F are as hereinbefore defined, with a compound of general formula

wherein $R_d$ has the meanings given for $R_5$ hereinbefore, with the exception of the hydrogen atom, or represents an $R_6CO-O-CHR_2-$ group, wherein $R_2$ and $R_6$ are as hereinbefore defined and $Z_3$ denotes a nucleophilic leaving group such as a halogen atom, e.g. chlorine or bromine.

The reaction is conveniently carried out in a solvent such as methylene chloride, tetrahydrofuran, dioxane, dimethylsulphoxide, dimethylformamide or acetone, optionally in the presence of a reaction accelerator such as sodium or potassium iodide and preferably in the presence of a base such as sodium carbonate, potassium carbonate or sodium hydroxide solution or in the presence of a tertiary organic base such as N-ethyl-diisopropylamine or N-methyl-morpholine, which may simultaneously serve as solvent, or optionally in the presence of silver carbonate or silver oxide at temperatures between $-30°$ and $100°$ C., but preferably at temperatures between $-10°$ and $80°$ C.

In the reactions described hereinbefore, any reactive groups present such as hydroxy, carboxy, amino, alkylamino or imino groups may be protected during the reaction by means of conventional protecting groups which are removed by cleaving after the reaction.

For example, the protective group for a hydroxy group may be a trimethylsilyl, acetyl, benzoyl, tert.butyl, trityl, benzyl or tetrahydropyranyl group, the protecting group for a carboxyl group may be a trimethylsilyl, methyl, ethyl, tert.butyl, benzyl or tetrahydropyranyl group, and the protecting group for an amino, alkylamino or imino group may be an acetyl, trifluoroacetyl, benzoyl, ethoxycarbonyl, tert.butoxycarbonyl, benzyloxycarbonyl, benzyl, methoxybenzyl or 2,4-dimethoxybenzyl group and for the amino group a phthalyl group may also be considered.

The optional subsequent cleaving of a protecting group may, for example, be carried out hydrolytically in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether cleaving, e.g. in the presence of iodotrimethylsilane, at temperatures between $0°$ and $100°$ C., preferably at temperatures between $10°$ and $50°$ C.

However, a benzyl, methoxybenzyl or benzyloxycarbonyl group may for example be cleaved hydrogenolytically, eg. using hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between $0°$ and $50°$ C., but preferably at ambient temperature, under a hydrogen pressure of 1 to 7 bar, preferably 3 to 5 bar.

A methoxybenzyl group may also be cleaved in the presence of an oxidising agent such as cerium(IV)ammonium nitrate in a solvent such as methylene chloride, acetonitrile or acetonitrile/water at temperatures between 0° and 50° C., but preferably at ambient temperature.

A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid, optionally using a solvent such as methylene chloride, dioxane or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20° and 50° C.

An allyloxycarbonyl group is cleaved by treating with a catalytic amount of tetrakis-(triphenylphosphine)palladium(O), preferably in a solvent such as tetrahydrofuran and preferably in the presence of an excess of a base such as morpholine or 1,3-dimedone, at temperatures between 0° and 100° C., preferably at ambient temperature and under inert gas, or by treating with a catalytic amount of tris-(triphenylphosphine)rhodium(I)chloride in a solvent such as aqueous ethanol and optionally in the presence of a base such as 1,4-diazabicyclo[2.2.2]octane at temperatures between 20° and 70° C.

Furthermore, the compounds of general formula I obtained may be resolved into their enantiomers and/or diastereomers as mentioned hereinbefore. Thus, for example, cis/trans mixtures may be resolved into their cis and trans isomers, and chiral compounds may be resolved into their enantiomers.

Thus, for example, the cis/trans mixtures obtained may be resolved by chromatography into the cis and trans isomers thereof and the compounds of general formula I which occur in racemate form may be separated by methods known per se (see Allinger N. L. and Eliel E. L. in "Topics in Stereochemistry", Vol. 6, Wiley Interscience, 1971) into their optical antipodes and compounds of general formula I having at feast 2 stereogenic centres may be separated on the basis of their physical-chemical differences using known methods, e.g. by chromatography and/or fractional crystallisation, into the diastereomers thereof, which, if they occur in racemic form, may subsequently be separated into the enantiomers as mentioned above.

The separation of enantiomers is preferably effected by column separation on chiral phases or by recrystallisation from an optically active solvent or by reacting with optically active substances, especially acid and the activated derivatives thereof, or alcohols which form salts or derivatives such as esters or amides with the racemic compound and separation of the diastereomeric salt mixture or derivative thus obtained, e.g. on the basis of their different solubilities, whilst the free antipodes may be released from the pure diastereomeric salts by the action of suitable agents. Particularly common, optically active acids include, for example, the D- and L-forms of tartaric acid, and dibenzoyltartaric acid, di-o-tolyl tartaric acid, malic acid, mandelic acid, camphorsulphonic acid, glutamic acid, aspartic acid and quinic acid. Examples of optically active alcohols include for example (+)- or (−)-menthol and examples of optically active acyl groups in amides include for example (+)- or (−)-menthyloxycarbonyl.

Moreover, the compounds of formula I obtained may be converted into the salts thereof, particularly for pharmaceutical use into the physiologically acceptable salts thereof with inorganic or organic acids. Examples of suitable acids include hydrochloric acid, hydrobromic acid, sulphuric acid, phosphoric acid, acetic acid, fumaric acid, succinic acid, lactic acid, citric acid, tartaric acid or maleic acid.

In addition, the new compounds of formula I thus obtained, if they contain a carboxyl group, may subsequently, if desired, be converted into the addition salts thereof with inorganic or organic bases, more particularly, for pharmaceutical use, into the physiologically acceptable addition salts thereof. Examples of suitable bases include sodium hydroxide, potassium hydroxide, ammonia, cyclohexylamine, ethanolamine, diethanolamine and triethanolamine.

The compounds used as starting materials are known from the literature in some cases or may be obtained by methods known from the literature (see Examples I to XXVI), e.g. by nucleophilic substitution reactions on aromatic compounds (see Jerry March in Advanced Organic Chemistry, Third Edition, John Wiley & Sons, pages 576–578 (1985) and Bunnett and Zahler in Chem. Rev. 49, 273–412 (1951)).

As already mentioned, the new carboxylic acid derivatives of general formula I and the addition salts thereof, particularly the physiologically acceptable addition salts thereof with inorganic or organic acids or bases, have valuable properties. Thus, the new compounds of general formula I wherein A contains an optionally substituted aminoalkyl, amino, amidino or guanidino group or a group which may optionally be converted in vivo into an aminoalkyl, amino, amidino or guanidino group, e.g. an aminoalkyl, amino, amidino or guanidino group which is substituted by an alkoxycarbonyl, benzyloxycarbonyl, allyloxycarbonyl or $R_1$—CO—O—($R_2$CH)—O—CO— group, and G denotes a carboxyl, phosphono, O-alkyl-phosphono or 5-tetrazolyl group or a group which may optionally be converted in vivo into a carboxyl, phosphono, O-alkyl-phosphono or 5-tetrazolyl group, e.g. a carbonyl group substituted by an $R_5O$— or $R_6$—CO—OCHR$_2$—O— group, have valuable pharmacological properties, and in addition to having an inhibitory effect on inflammation and bone degradation, they have in particular antithrombotic, antiaggregatory and tumour- or metastasis-inhibiting effects.

By way of example, the compounds of general formula I were investigated for their biological effects as follows:

1. Competitive binding of $^3$H-BIBU 52/test substance to human thrombocytes:

A suspension of human thrombocytes in plasma is incubated with $^3$H-BIBU 52 [=(3S,5S)-5-[(4'-amidino-4-biphenylyl)oxymethyl]-3-[(carboxyl)methyl]-2-pyrrolidinone[3-$^3$H-4-biphenylyl]] (see German Patent Application P 42 14 245.8 of the same applicant, dated 30.04.1992, internal reference: Case 5/1093-FL), which replaces the $^{125}$I fibrinogen ligand known from the literature and various concentrations of the substance to be tested. The free and bound ligand is separated by centrifuging and quantified by scintillation counting. The inhibition of $^3$H-BIBU 52 binding by the test substance is determined from the measurements obtained.

In order to do this, donor blood is taken from an anticubital vein and anticoagulated with trisodium citrate (final concentration 13 mM). The blood is centrifuged for 10 minutes at 170×g and the supernatant platelet-rich plasma (PRP) is removed. The remaining blood is vigorously centrifuged once more in order to obtain plasma. The PRP is diluted 1:10 with autologous plasma. 750 μl are incubated with 50 μl of physiological saline solution, 100 μl of test substance solution, 50 μl of $^{14}$C-sucrose (3,700 Bq) and 50 μl of $^3$H-BIBU 52 (final concentration: 5 nM) at ambient temperature for 20 minutes. In order to measure the non-specific binding, 5μl of BIBU 52 (final concentration: 30 μM) are used instead of the test substance. The samples are centrifuged for 20 seconds at 10,000×g and the supernatant is poured off. 100 μl thereof are measured in order to determine the free ligand. The pellet is dissolved in 500 μl of 0.2N NaOH, 450 μl are mixed with 2 ml of scintillator and 25 μl of 5N HCl and measured. The residual plasma remaining in the pellet is determined from the $^{14}$C-content and the bound ligand is determined from the $^3$H-measurement. After the non-specific binding has been deducted, the pellet activity is plotted against the concentration of the test substance and the concentration for 50% inhibition of binding is determined. 2. Antithrombotic activity

Method

The thrombocyte aggregation is measured using the method of Born and Cross (J. Physiol. 170: 397 (1964)) in platelet-rich plasma taken from healthy volunteers. To inhibit coagulation the blood is mixed with 3.14% sodium citrate in a volume ratio of 1:10.

Collagen-Induced Aggregation

The pattern of the decrease in optical density of the platelet suspension is photometrically measured and recorded after the addition of the aggregation-triggering substance. The rate of aggregation is determined from the angle of inclination of the density curve. The point on the curve where there is maximum light transmittance is used to calculate the optical density.

The concentration of collagen used is as small as possible but sufficient to produce an irreversible reaction curve. Standard commercial collagen produced by Hormonchemie of Munich is used. Before the addition of the collagen the plasma is incubated for 10 minutes with the substance at 37° C. From the concentration/activity curve an $EC_{50}$ is determined, which describes the concentration giving a 50% change in the optical density in terms of the inhibition of aggregation.

The following table shows the results which were obtained:

| Substance (Example No.) | Competitive binding of $^3$H-BIBU 52/test substance to human thrombocytes $IC_{50}$ [nM] | Inhibition of platelet aggregation $EC_{50}$ [nM] |
| --- | --- | --- |
| 1(1) | 870.0 | 110 |
| 1(5) | 1200.0 | 80 |
| 1(9) | 17000.0 | 90 |
| 1(24) | 4400.0 | 220 |
| 1(25) | 30000.0 | 6800 |
| 2 | 7.4 | 40 |
| 2(1) | 18.0 | 40 |
| 2(2) | 47.0 | 90 |
| 2(3) | 4.5 | 30 |
| 2(6) | 1.5 | 40 |
| 2(7) | 29.0 | 80 |
| 2(8) | 27.0 | 60 |
| 2(11) | 230.0 | 380 |
| 2(17) | 44.0 | 130 |
| 2(19) | 370.0 | 620 |
| 2(22) | 310.0 | 680 |
| 2(42) | 100.0 | 170 |
| 3 | 130.0 | 230 |
| 3(1) | 230.0 | 660 |
| 3(2) | 14.0 | 100 |
| 3(4) | 78.0 | 100 |
| 3(12) | 180.0 | 290 |
| 3(15) | 5.7 | 30 |
| 3(17) | 74.0 | 180 |
| 3(24) | 9.1 | 110 |
| 3(25) | 4.0 | 52 |
| 3(26) | 12.0 | 65 |
| 4 | 5300.0 | 4300 |
| 7 | 1200.0 | 280 |
| 7(2) | 2100.0 | 360 |
| 8 | 540.0 | 190 |

The inhibition of thrombocyte aggregation after oral administration of the test substance is determined ex vivo on Rhesus monkeys.

Directly before the oral administration of the test substance suspended in Natrosol, a blood sample is taken from the cubital vein of the animals to provide a reference value. At specified times after the administration of the substance, fresh blood samples are taken and investigated as follows.

The whole blood mixed with 3.14% sodium citrate in a ratio by volume of 1:10 is centrifuged at 200×g for 15 minutes. The supernatant, platelet-rich plasma, is carefully removed. From the sediment which is rich in erythrocytes, the platelet-poor plasma is obtained as supernatant, by centrifuging at 4000×g for 10 minutes.

The thrombocyte aggregation triggered with collagen (Hormonchemie, Munich; 2 μg/ml final concentration in platelet-rich plasma) in these ex vivo samples is measured photometrically using the method of Born and Cross (J. Physiol. 170, 397 (1964)). The maximum light transmittance of the platelet-rich plasma, measured after collagen stimulation, is compared with the reference value in order to determine the inhibition of aggregation at the various times of blood sampling after the administration of the substance, relative to the reference value.

The compound of Example 1(24) inhibits the collagen-induced thrombocyte aggregation ex vivo after the oral administration of 1 mg/kg for more than 4 hours.

The compounds according to the invention are well tolerated because after intravenous administration of 30 mg/kg of the compounds of Examples 2, 2(7), 2(8), 3 and 5 to three mice in each case, no animals died.

In the light of their inhibitory effect on cell-cell or cell-matrix interactions, the new carboxylic acid derivatives of general formula I and the physiologically acceptable addition salts thereof are suitable for combating or preventing diseases in which smaller or greater cell aggregates occur or in which cell-matrix interactions play a part, e.g. in treating or preventing venous and arterial thrombosis, cerebrovascular diseases, lung embolism, cardiac infarction, arteriosclerosis, osteoporosis and the metastasis of tumours and the treatment of genetically caused or acquired disorders of cell interactions with one another or with solid structures. They are also suitable for parallel therapy in thrombolysis with fibrinolytics or vascular interventions such as transluminal angioplasty or in the treatment of shock, psoriasis, diabetes and inflammation.

For treating or preventing the diseases mentioned above, the dosage is between 0.1 μg and 30 mg/kg of body weight, preferably 1 μg to 15 mg/kg of body weight, given in up to 4 doses per day. For this purpose the compounds of formula I produced according to the invention, optionally in conjunction with other active substances such as thromboxane receptor antagonists and thromboxane synthesis inhibitors or combinations thereof, serotonin antagonists, α-receptor antagonists, alkylnitrates such as glycerol trinitrate, phospho-diesterase inhibitors, prostacyclin and the analogues thereof, fibrinolytics such as tPA, prourokinase, urokinase, streptokinase, or anticoagulants such as heparin, dermatane sulphate, activated protein C, vitamin K antagonists, hirudine, inhibitors of thrombin or other activated clotting factors, may be incorporated together with one or more inert conventional carriers and/or diluents, e.g. corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof, into conventional galenic preparations such as plain or coated tablets, capsules, powders, suspensions, solutions, sprays or suppositories.

The Examples which follow are intended to illustrate the invention:

Preparation of the starting products:

EXAMPLE I 1-(4-Cyanophenyl)-piperazine 5.0 g of 4-fluorobenzoic acid nitrile and 17.8 g of piperazine are stirred at 110° C. for 4 hours. The cooled mixture is dissolved in water and the aqueous phase is extracted with ethyl acetate. The organic phase is washed with saturated saline solution, dried over sodium sulphate and the solvent is removed under reduced pressure. The residue remaining is chromatographed over silica gel.

Yield: 7.0 g (91% of theory), $R_f$ value: 0.31 (silica gel; methylene chloride/methanol/conc. ammonia=9:1:0.1)

EXAMPLE II 1-(4-Cyanophenyl)-4-[[trans-4-(methoxycarbonyl)-cyclohexyl]-aminocarbonyl]-piperazine To a suspension of 4.85 g of p-nitrophenylchloroformate and 4.65 g of methyl-trans-4-amino-cyclohexanecarboxylate hydrochloride in 200 ml of tetrahydrofuran, at 0° C., a solution of 10 ml of triethylamine in 50 ml of tetrahydrofuran is added dropwise. The mixture is stirred for 2.5 hours at 0° C. and then 4.5 g of 1-(4-cyanophenyl)-piperazine are added. The mixture is stirred for 16 hours at ambient temperature and heated to 50° C. for 4 hours. Under reduced pressure, approx. 200 ml of tetrahydrofuran are evaporated off and the residue is dissolved in ethyl acetate. The organic phase is washed twice with 1N sodium hydroxide solution and once with saturated saline solution and dried over sodium sulphate. The solvent is removed under reduced pressure and the crude product is chromatographed over silica gel using ethyl acetate as eluant.

Yield: 6.0 g (65% of theory), Melting point: 177°–179° C. $R_f$ value: 0.67 (silica gel; methylene chloride/methanol/conc. ammonia=9:1:0.1)

The following compounds are obtained analogously to Example II:

(1) 1-(5-cyanopyrid-2-yl)-4-[[trans-4-(methoxycarbonyl)-cyclohexyl]-aminocarbonyl]-piperazine 1-(5-cyanopyrid-2-yl)-piperazine is used. The crude product is triturated with ethyl acetate and the precipitate is suction filtered and dried. Melting point: 176°–179° C. $R_f$ value: 0.50 (silica gel; methylene chloride/methanol/conc. ammonia=9:1:0.1)

(2) 4-(4-cyanophenyl-1-[[trans-4-(methoxycarbonyl)-cyclohexyl]-aminocarbonyl]-piperidine 4-(4-cyanophenyl)-piperidine-hydrochloride is used. Melting point: 136°–138° C. $R_f$ value: 0.32 (silica gel; ethyl acetate/cyclohexane=4:1)

EXAMPLE III 1-(4-Cyanophenyl)-4-[N-[trans-4-(methoxycarbonyl)-cyclohexyl]-N-methyl-aminocarbonyl]-piperazine A solution of 2.50 g of 1-(4-cyanophenyl)-4-[[trans-4-(methoxycarbonyl)-cyclohexyl]-aminocarbonyl]-piperazine and 0.76 g of potassium tert.butoxide in 30 ml of dimethylsulphoxide is stirred for 30 minutes at ambient temperature. Then 0.5 ml of methyliodide is added dropwise and the mixture is stirred for 1.5 hours at ambient temperature. The reaction solution is diluted with 100 ml of water and the aqueous phase is extracted three times with ethyl acetate. The organic phases are washed with saturated saline solution and dried over sodium sulphate. The solvent is removed under reduced pressure and the residue remaining is chromatographed over silica gel with ethyl acetate/cyclohexane (3:1) as eluant. Yield: 1.0 g (39% of theory). The product contains about 20% of cis compound $R_f$ value: 0.58 (silica gel; ethyl acetate) 1.0 g of starting material are obtained as a further fraction. $R_f$ value: 0.45 (silica gel; ethyl acetate)

The following compounds are obtained analogously to Example III:

(1) 1-(5-cyanopyrid-2-yl)-4-[N-[trans-4-(methoxycarbonyl)-cyclohexyl]-N-methyl-aminocarbonyl]-piperazine $R_f$ value: 0.56 (silica gel; ethyl acetate)

(2) 4- (4-cyanophenyl) -1- [N- [trans-4-(methoxycarbonyl)-cyclohexyl]-N-methyl-aminocarbonyl]-piperidine $R_f$ value: 0.57 (silica gel; ethyl acetate/cyclohexane=4:1)

(3) 1-(4-cyanophenyl)-4-[N-(3-methoxycarbonylpropyl)-N-methyl-aminocarbonyl]-piperidine (4) 1-(4-cyanophenyl)-4-[N-(3-methoxycarbonylpropyl)-N-benzyl-aminocarbonyl]-piperidine Using benzylbromide as alkylating reagent.

(5) 1-(4-cyanophenyl)-4-[N-(3-methoxycarbonylpropyl)-N-(2-phenylethyl)-aminocarbonyl]-piperidine Using 2-phenylethyliodide as alkylating reagent.

(6) 1-(4-cyanophenyl]-4-[N-(3-methoxycarbonylpropyl)-N-(3-phenylpropyl)-aminocarbonyl]-piperidine Using 3-phenylpropyliodide as alkylating reagent.

(7) 1-(4-cyanophenyl)-4-[N-(3-methoxycarbonylpropyl)-N-(n-pentyl)-aminocarbonyl]-piperidine Using n-pentyliodide as alkylating reagent.

(8) 1-(4-cyanophenyl)-4-[N-(2-methoxycarbonylethyl)-N-methyl-aminocarbonylmethyl]-piperidine (9) 1-(4-cyanophenyl)-4-[N-(2-methoxycarbonylethyl)-N-(2-phenylethyl)-aminocarbonylmethyl]-piperidine Using 2-phenylethyliodide.

(10) 1-(4-cyanophenyl)-4-[N-[trans-4-(methoxycarbonyl)-cyclohexyl]-N-methyl-aminocarbonyl]-piperidine

(11) 1-(4-cyanophenyl)-4-[N-(2-methoxycarbonylethyl)-N-(2-phenylethyl)-aminocarbonylmethyl]-piperazine

(12) 1-(4-cyanophenyl)-4-[(4-trans-methoxycarbonylcyclohexyl)-carbonylmethylamino]-piperidine

EXAMPLE IV

6-Bromonicotinic acid nitrile 38.0 g of 6-chloronicotinic acid amide and 5.0 g of phosphorusoxybromide are stirred for 4 hours at 100° C. The reaction solution is stirred in batches into 1 liter of water. The precipitate is suction filtered, washed with water and dried. Yield: 40.0 g (90% of theory), $R_f$ value: 0.91 (silica gel; methylene chloride/methanol=15:1)

EXAMPLE V 1-(5-Cyanopyrid-2-yl)-piperazine 0.6 g of 6-bromonicotinic acid nitrile and 22.6 g of piperazine in 50 ml of dimethylformamide are stirred for 2 hours at 80° C. The solvent is removed under reduced pressure, the residue is suspended in water and the aqueous phase is extracted with ethyl acetate. The organic phase is washed with saturated saline solution, dried over sodium sulphate and the solvent is removed under reduced pressure. The residue remaining is chromatographed over silica gel. Yield: 8.0 g (81% of theory), Melting point: 73°–75° C. $R_f$ value: 0.27 (silica gel; methylene chloride/methanol/conc. ammonia=9:1:0.1)

EXAMPLE VI

4-Carboxy-1-(5-cyanopyrid-2-yl)-piperidine

A suspension of 1.8 g of 6-bromonicotinic acid nitrile, 1.3 g of 4-piperidinylcarboxylic acid and 1.06 g of sodium carbonate in 15 ml of dimethylformamide is stirred for 2 hours at 120° C. After cooling, the suspension is diluted with water. 2.0 g of ammonium chloride are added and the aqueous phase is extracted with ethyl acetate. The organic phase is washed with saturated saline solution, dried over sodium sulphate and the solvent is removed under reduced pressure. Yield: 1.2 g (52% of theory), $R_f$ value: 0.29 (silica gel; methylene chloride/methanol/conc. ammonia=4:1:0.25)

EXAMPLE VII 1-(5-Cyanopyrid-2-yl)-4-[4-(methoxycarbonylmethyl)-piperidinocarbonyl]-piperidine 2.3 g of 4-carboxy-1-(5-cyanopyrid-2-yl)-piperidine, 2.0 g of methyl 4-piperidylacetate hydrochloride, 4.8 g of 2-[(1H)-benzotriazol-1-yl]-1,1,3,3-tetramethyl-uronium tetrafluoroborate and 5 ml of triethylamine in 75 ml of dimethylformamide is stirred at ambient temperature for 16 hours. The solvent is removed under reduced pressure. The residue is diluted with water and the aqueous phase is extracted with ethyl acetate. The organic phase is washed with water and saturated saline solution and dried over sodium sulphate. The solvent is removed under reduced pressure and the residue is chromatographed over silica gel. Yield: 2.75 g (74% of theory), Melting point: 112°–115° C. $R_f$ value: 0.40 (silica gel; methylene chloride/methanol=15:1)

The following compounds are obtained analogously to Example VII:

(1) 1-(5-cyanopyrid-2-yl)-4-[N-[trans-4-(methoxycarbonyl)-cyclohexyl]-aminocarbonyl]-piperidine $R_f$ value: 0.39 (silica gel; methylene chloride/methanol=15:1)

(2) 1-(4-cyanophenyl)-4-[N-(2-methoxycarbonylethyl)-aminocarbonylmethyl]-piperazine Melting point: 89°–92° C.

(3) 1-(4-cyanophenyl)-4-[(3-methoxycarbonylpropyl)-carbonylamino]-piperidine Prepared from 4-amino-1-(4-cyanophenyl)-piperidine and monomethyl glutarate.

(4) 1-(4-cyanophenyl)-4-[(4-trans-methoxycarbonylcyclohexyl)-carbonylamino]-piperidine Prepared from 4-amino-1-(4-cyanophenyl)-piperidine and the monomethyl ester 1,4-trans-cyclohexane dicarboxylic acid.

EXAMPLE VIII 4-(4-Carboxyphenyl)-piperidine-hydrochloride

To a solution of 63.0 g of 1-acetyl-4-phenyl-piperidine in 1000 ml of methylene chloride, 157.4 g of oxalyl chloride are added dropwise with thorough stirring at −10° to −20° C. Then 46.7 g of aluminum chloride are added. The mixture is stirred for 1 hour at −10° C. and a further 82.7 g of aluminium chloride are added. After a further 2 hours the cooling bath is removed and the mixture is stirred for 24 hours at ambient temperature. The reaction solution is carefully stirred into about 4 liters of ice/water and the aqueous phase is extracted twice with methylene chloride. The combined organic phases are washed with water, dried over sodium sulphate and the solvent is removed under reduced pressure. The residue remaining is dissolved in 2.5 liters of 2N sodium hydroxide solution, with vigorous stirring. Ice is added to the dark aqueous solution which is then acidified with conc. hydrochloric acid. The precipitate is suction filtered, washed with water and refluxed for 5 hours in 2 liters of 6N hydrochloric acid. The solvent is removed under reduced pressure. The solid remaining is triturated with a little water and suction filtered. Yield: 40.5 g (54% of theory), Melting point: >300° C. $R_f$ value: 0.07 (silica gel; methylene chloride/methanol/conc. ammonia=4:1:0.25)

EXAMPLE IX 1-tert. Butyloxycarbonyl-4-(4-carboxyphenyl)-piperidine

To 16.4 g of sodium hydroxide in 300 ml of water, 47.5 g of 4-(4-carboxyphenyl)-piperidine-hydrochloride are carefully added. The suspension is diluted with 500 ml of dioxane and 250 ml of water. Then, 54.6 g of di-tert.butylpyrocarbonate are added batch-wise. The mixture is stirred for 16 hours at ambient temperature. The precipitate is suction filtered and the filtrate is partially evaporated under reduced pressure. The precipitate and the remaining aqueous filtrate are combined and diluted with 1 liter of water. The aqueous phase is adjusted to pH 2 with saturated potassium hydrogen sulphate solution and extracted twice with ethyl acetate. The combined ethyl acetate phases are washed with saturated saline solution, dried over sodium sulphate and the solvent is removed under reduced pressure. The crude crystalline product is triturated with a little ethyl acetate, suction filtered and dried. Yield: 54.0 g (90% of theory), Melting point: 172°–174° C. $R_f$ value: 0.73 (silica gel; ethyl acetate/cyclohexane=4:1)

EXAMPLE X 4-(4-Aminocarbonylphenyl)-1-tert.butyloxycarbonyl-piperidine

To a solution of 21.4 g of 1-tert.butyloxycarbonyl-4-(4-carboxyphenyl)-piperidine in 250 ml of anhydrous dimethylformamide are added, at −10° C., 9.5 g of 1-hydroxy-(1H)-benzotriazole and 17.3 g of N,N'-dicyclohexylcarbodiimide. The mixture is stirred for 15 minutes at −10° C. and the temperature is allowed to come up to ambient temperature within 1 hour. Then at −10° C. 20 ml of conc. ammonia are added dropwise with vigorous stirring. The mixture is stirred for 1 hour at −10° C. and for a further 2 hours at ambient temperature. The solvent is removed under reduced pressure. The residue remaining is suspended in water and the aqueous phase is extracted four times with ethyl acetate. The combined ethyl acetate phases are filtered, the filtrate is dried over sodium sulphate and the solvent is removed under reduced pressure. The residue remaining is chromatographed over silica gel. Yield: 17.5 g (82% of theory), Melting point: 188°–191° C. $R_f$ value: 0.36 (silica gel; ethyl acetate/cyclohexane=4:1)

EXAMPLE XI 1-tert. Butyloxycarbonyl-4-(4-cyanophenyl)-piperidine

A solution of 4.5 g of 4-(4-aminocarbonylphenyl)-1-tert.butyloxycarbonyl-piperidine, 6.8 g of triphenylphosphine, 2.4 g of carbon tetrachloride and 1.6 g of triethylamine in 50 ml of chloroform is stirred for 2 hours at 60° C. 1 ml of carbon tetrachloride is added dropwise and the mixture is stirred for a further 3 hours at 60° C. The solvent is removed under reduced pressure and the remaining oil is chromatographed over silica gel. Yield: 2.4 g (57% of theory), $R_f$ value: 0.32 (silica gel; cyclohexane/ethyl acetate=4:1)

EXAMPLE XII 4-(4-Cyanophenyl)-piperidine-hydrochloride

A solution of 2.4 g of 1-tert.butyloxycarbonyl-4-(4-cyanophenyl)-piperidine in 20 ml of dioxane and 20 ml of ethereal hydrochloric acid is stirred for 16 hours at ambient temperature. The crystalline precipitate is suction filtered, washed with ether and dried. Yield: 1.85 g (99% of theory), Melting point: 284°–288° C. $R_f$ value: 0.79 (silica gel; methylene chloride/methanol/conc. ammonia=4:1:0.25)

EXAMPLE XIII

1-Methoxycarbonylmethyl-4-[(4-nitrophenyl)-oxycarbonyl]-piperidine

To a suspension of 2.91 g of methyl piperid-4-yl-acetate-hydrochloride and 3.02 g of 4-nitrophenyl-chloroformate in 150 ml of tetrahydrofuran, a solution of 3.54 g of triethylamine in 10 ml of tetrahydrofuran is added dropwise at 0° C. The mixture is stirred for 3 hours at 0° C. Then the cooling bath is removed and the mixture is stirred for 16 hours at ambient temperature. The precipitate is suction filtered and the filtrate is removed under reduced pressure. The residue remaining is chromatographed over silica gel. The still unpurified product is dissolved in ethyl acetate and the organic phase is washed once with 0.5N sodium hydroxide solution and once with water. The organic phase is dried over sodium sulphate and the solvent is removed under reduced pressure. Yield: 3.30 g (68% of theory), Melting point: 109°–111° C. $R_f$ value: 0.63 (silica gel; ethyl acetate/cyclohexane=1:1)

EXAMPLE XIV 4-(4-Cyanophenyl)-1-[4-(methoxycarbonylmethyl)-piperidinocarbonyl]-piperidine 1.3 g of 4-(4-cyanophenyl)-piperidine and 2.9 g of 4-(methoxycarbonylmethyl)-1-[(4-nitrophenyl)-oxycarbonyl]-piperidine are stirred at 140° C. for 2.5 hours. The mixture is left to cool and the residue is dissolved in ethyl acetate. The organic phase is washed twice with 0.5N sodium hydroxide solution and once with water. The ethyl acetate phase is dried over sodium sulphate and the solvent is removed under reduced pressure. The residue remaining is chromatographed over silica gel. Yield: 1.5 g (58% of theory), Melting point: 115°–118° C. $R_f$ value: 0.32 (silica gel; ethyl acetate/cyclohexane=1:1)

The following compounds are obtained analogously to Example XIV:

(1) 1-(4-cyanophenyl)-4-[4-(methoxycarbonylmethyl)piperidinocarbonyl]-piperazine Melting point: 99°–100° C.

(2) 1-(4-cyanophenyl)-4-[4-(ethoxycarbonylmethylidene)-piperidinocarbonyl]-piperazine (A) and 1-(4-cyanophenyl)-4-[4-(ethoxycarbonylmethyl)-3,4-dehydro-piperidinocarbonyl]-piperazine (B) as a mixture. 1-(4-cyanophenyl)-piperazine is reacted with a mixture of 1-[(4-nitrophenyl)-oxycarbonyl]-4-(ethoxycarbonylmethylidene)piperidine and 1-[(4-nitrophenyl)-oxycarbonyl]-4-(ethoxycarbonylmethylidene)-3,4-dehydropiperidine. The subsequent separation is carried out using silica gel. $R_f$ value of (A): 0.55 (silica gel; methylene chloride/ethyl acetate=9:1)

$R_f$ value of (B): 0.42 (silica gel; methylene chloride/ethyl acetate=9:1)

EXAMPLE XV 1-(4-Cyanophenyl)-4-[N-[cis-4-(methoxycarbonyl)-cyclohexyl]-N-methyl-aminocarbonyl]-piperazine To a suspension of 2.5 g of methyl cis-4-(methylamino)-cyclohexanecarboxylate hydrochloride and 2.4 g of p-nitrophenylchloroformate in 100 ml of tetrahydrofuran, a solution of 4 ml of triethylamine in 20 ml of tetrahydrofuran is added dropwise at 0° C. The resulting mixture is stirred for 3 hours at 0° C and then the solvent is removed under reduced pressure. The residue remaining is dissolved in ethyl acetate and the organic phase is washed with 1N sodium hydroxide sulting mixture is stirred for 3 hours at 0° C. and then with saturated saline solution. The organic phase is dried over sodium sulphate and the solvent is removed under reduced pressure. To the remaining residue 2.2 g of 1-(4-cyanophenyl)-piperazine is added and the resulting mixture is stirred for 6 hours at 140° C. The residue is dissolved in ethyl acetate and the organic phase is washed with 1N sodium hydroxide solution, with saturated saline solution, with 1N hydrochloric acid and with saturated saline solution. The organic phase is dried over sodium sulphate and the solvent is eliminated under reduced pressure. The crude product is dissolved in a little boiling ethyl acetate. After the addition of cyclohexane, the mixture is allowed to cool and the precipitate is removed by suction filtering. Yield: 1.9 g (34% of theory), $R_f$ value: 0.70 (silica gel; methylene chloride/methanol/conc. ammonia=9:1:0.1)

The following compound is obtained analogously to Example XV:

(1) 1-(4-cyanophenyl)-4-[N-benzyl-N-[trans-4-(methoxycarbonyl)-cyclohexyl]-aminocarbonyl]-piperazine The crude product is chromatographed over silica gel. $R_f$ value: 0.61 (silica gel; methylene chloride/methanol=15:1)

EXAMPLE XVI

4-Carboxy-1-(4-cyanophenyl)-piperidine 1.2 g of 4-fluorobenzonitrile and 1.07 g of 4-piperidylcarboxylic acid are heated to 150° C. in 20 ml of dimethylsulphoxide for 4 hours. After cooling, the dark solution is diluted with a 0.5N potassium hydrogen sulphate solution and the aqueous phase is exhaustively extracted with ethyl acetate. The combined organic extracts are dried and the solvent is removed under reduced pressure. The residue remaining is triturated with ether, suction filtered and dried. Yield: 0.86 g (45% of theory), Melting point: 230°–234° C. (decomp.)

The following compound is obtained analogously to Example XVI:

(1) 1-(4-cyanophenyl)-4-tert.butyloxycarbonylamino-piperidine By reacting 4-fluorobenzonitrile with 4-tert-.butyloxy-carbonylamino-piperidine

EXAMPLE XVII 1-(4-Cyanophenyl)-4-[4-(methoxycarbonylmethyl)-piperidinocarbonyl]-piperidine To a solution of 3.6 g of 4-carboxy-1-(4-cyanophenyl)-piperidine in 100 ml of tetrahydrofuran and 20 ml of dimethylformamide, 2.8 g of N,N'-carbonyl-diimidazole are added batch-wise at ambient temperature and the mixture is stirred for 1 hour. Then, 3.35 g of methyl 4-piperidyl-acetate hydrochloride and 1.9 ml of N-methyl-morpholine are added and the mixture is stirred for 16 hours at ambient temperature. The solvent is removed under reduced pressure and the residue is taken up in water and methylene chloride. By the addition of 2N hydrochloric acid, the mixture is acidified to pH 6, the organic phase is separated off and the aqueous phase is extracted twice with methylene chloride. The combined methylene chloride phases are dried and the solvent is removed under reduced pressure. The residue is triturated with ether, suction filtered and dried. Yield: 4.1 g (71% of theory), Melting point: 110°–112° C.

The following compounds are obtained analogously to Example XVII:

(1) 1-(4-cyanophenyl)-4-[4-(ethoxycarbonylmethylidene)-piperidinocarbonyl]-piperidine Using 4-(ethoxycarbonylmethylidene)-piperidine. Oil (2) 1-(4-cyanophenyl)-4-[4-(ethoxycarbonylmethyl)-3,4-dehydropiperidinocarbonyl]-piperidine Using 4-(ethoxycarbonylmethyl)-3,4-dehydropiperidine. Oil (3) 1-(4-cyanophenyl)-4-[N-[trans-4-(methoxycarbonyl)-cyclohexyl]-aminocarbonyl]-piperidine Using methyl trans-4-amino-cyclohexanecarboxylate. Melting point: 230°–232° C.

EXAMPLE XVIII 1-(4-Cyanophenyl)-4-(methoxycarbonylmethyl)-piperazine 2 g of 1-(4-cyanophenyl)-piperazine are stirred in 20 ml of dry dimethylformamide at ambient temperature with 0.51 g of a 50% sodium hydride/oil suspension. Whilst cooling in a water bath, 1 ml of bromoacetate is added. Then the mixture is diluted with water and extracted with ethyl acetate. The combined ethyl acetate extracts are dried and the solvent is removed under reduced pressure. The residue remaining is chromatographed with methylene chloride/methanol (98:2) over silica gel. The product is triturated with ether, suction filtered and washed with petroleum ether. Yield: 1.6 g (58% of theory), Melting point: 92°–96° C.

EXAMPLE XIX 1-(Carboxymethyl)-4-(4-cyanophenyl)-piperazine

To 3 g of 1-(4-cyanophenyl)-4-(methoxycarbonylmethyl)-piperazine in 46 ml of tetrahydrofuran 58 ml of a 1 molar aqueous lithium hydroxide solution are added, at ambient temperature and with stirring, and the reaction solution is left to stand for 3 hours at ambient temperature. Then 3.2 g of ammonium chloride are added and the tetrahydrofuran is distilled off under reduced pressure. The precipitate is suction filtered, washed with water and dried. Yield: 2.2 g (77% of theory), Melting point: over 300° C. $R_f$ value: 0.18 (silica gel; methylene chloride/methanol=9:1)

EXAMPLE XX

4-Hydroxymethyl-piperidine-hydrochloride 25 g of 4-pyridylmethanol are hydrogenated in 300 ml of 50% acetic acid in the presence of 2 g of platinum dioxide at ambient temperature and under a hydrogen pressure of 60 psi. After the uptake of hydrogen has ceased and the catalyst has been removed, the solvent is removed under reduced pressure. The solid residue is taken up in ether and then the hydrochloride is precipitated with ethereal hydrochloric acid. The precipitate is suction filtered and dried. Yield: 28.3 g (82% of theory), Melting point: 120°–125° C.

EXAMPLE XXI 1-(4-Cyanophenyl)-4-hydroxymethyl-piperidine

A solution of 12.2 g of 4-hydroxymethyl-piperidine-hydrochloride, 9.8 g of 4-fluorobenzonitrile and 28.3 ml of N-ethyl-diisopropylamine is heated to 140° C. for 4 hours. After cooling, it is chromatographed over silica gel using methylene chloride and methylene chloride-/ethyl acetate (1:1) as eluant. After the solvent has been removed under reduced pressure the residue remaining is triturated with petroleum ether and suction filtered. Yield: 5.1 g (29% of theory), Melting point: 148°–150° C.

EXAMPLE XXII 1-(4-Cyanophenyl)-4-mesyloxymethyl-piperidine

To a solution of 5.5 g of 1-(4-cyanophenyl)-4-hydroxymethyl-piperidine and 5.16 g of triethylamine in 150 ml of methylene chloride, 5.84 g of methanesulphonic acid chloride are slowly added dropwise at ambient temperature and with stirring. After it has all been added the mixture is left to stand overnight and the solvent is removed under reduced pressure. The residue is chromatographed with methylene chloride/methanol (50:1) over silica gel. Yield: 6.95 g (93% of theory), Mass spectrum: $(M+H)^+ = 295$

EXAMPLE XXIII

Mixture of 1-(4-cyanophenyl)-4-iodomethyl-piperidine and 1-(4-cyanophenyl)-1-aza-bicyclo[2.2.1]heptanyliumiodide A solution of 6.8 g of 1-(4-cyanophenyl)-4-mesyloxymethyl-piperidine and 17.4 g of sodium iodide in 100 ml of acetone is refluxed for 6 hours. The solvent is removed under reduced pressure and the residue remaining is heated to boiling with 300 ml methylene chloride. The mixture is filtered and the filtrate is evaporated to dryness under reduced pressure. The residue is crystallised from ethanol/petroleum ether. (A solution of these crystals consists of a mixture of 1-(4-cyanophenyl)-4-iodomethyl-piperidine and 1-(4-cyanophenyl)-1-aza-bicyclo[2.2.1]-heptanylium-iodide, the quantitative composition being dependent on the temperature, concentration and solvent). Yield: 5.9 g (78% of theory), Mass spectrum: $M^+ = 326$

EXAMPLE XXIV 1-(4-Cyanophenyl)-4-[4-(methoxycarbonylmethyl)-piperidinomethyl]-piperidine A suspension of 2.18 g of 1-(4-cyanophenyl)-4-iodomethyl-piperidine (mixture from Example XXV), 1.26 g of methyl-4-piperidyl-acetate-hydrochloride and 1.35 g of triethylamine in 150 ml of dimethylformamide is heated to 130° C. for 24 hours. After cooling, the solvent is removed under reduced pressure and the residue is chromatographed over silica gel with methylene chloride/methanol (30:1). The solvent is removed under reduced pressure and the crude product is used for the next stage of synthesis without any further purification.

The following compounds are obtained analogously:

(1) 1-(4-cyanophenyl)-4-[N-[trans-4-(methoxycarbonyl)-cyclohexyl]-aminomethyl]-piperidine By reacting with methyl trans-4-amino-cyclohexane-carboxylate at 60° C.

(2) 1-(4-cyanophenyl)-4-[N-[trans-4-(methoxycarbonyl)-cyclohexyl]-N-methyl-aminomethyl]-piperidine By reacting with methyl trans-4-methylaminocyclohexane-carboxylate.

(3) 1-(4-cyanophenyl)-4-[4-(methoxycarbonylmethylidene)-piperidinomethyl]-piperidine By reacting with 4-methoxycarbonylmethylidene-piperidine at 90° C.

EXAMPLE XXV

N-[trans-4-(methoxycarbonyl)-cyclohexyl]-N-(3-phenylpropyl)-amine-hydrochloride

A solution of 2 g of methyl trans-4-aminocyclohexane-carboxylate-hydrochloride, 1.5 ml of 3-phenylpropionaldehyde and 1.3 g of sodium cyanoborohydride in 40 ml of dry methanol is stirred for 20 hours at ambient temperature. The mixture is diluted with water and extracted with ethyl acetate. The combined ethyl acetate phases are dried, acidified with ethereal hydrochloric acid and the solvent is removed under reduced pressure. The residue is triturated with acetone, suction filtered and washed with acetone and then with ether. Yield: 1.9 g (59.1% of theory), Melting point: 258°–260° C.

EXAMPLE XXVI 1-(4-Cyanophenyl)-4-[N-[trans-4-(methoxycarbonyl)-cyclohexyl]-N-(3-phenylpropyl)-aminocarbonyl]-piperidine A solution of 1.37 g of 4-carboxy-1-(4-cyanophenyl)-piperidine, 1.85 g of N-[trans-4-(methoxycarbonyl)-cyclohexyl]-N-(3-phenylpropyl)-amine-hydrochloride, 0.88 g of 1-hydroxy-(1H)-benzotriazole, 2.1 g of 2-[(1H)-benzotriazol-1-yl]-1,1,3,3-tetramethyl-uronium-tetrafluoroborate and 1.43 ml of N-methyl-morpholine in 40 ml of dimethylformamide is heated to 60° C. for 6 hours. After cooling, the mixture is diluted with sodium bicarbonate solution and the aqueous phase is extracted with ethyl acetate. The combined ethyl acetate phases are washed with dilute citric acid solution and then with a dilute sodium bicarbonate solution and dried and the solvent is removed under reduced pressure. The residue is chromatographed with methylene chloride and methylene chloride/methanol (8:2) over silica gel. Yield: 0.55 (19% of theory), Melting point: 145°–146° C.

The following compounds are obtained analogously to Example XXVI:

(1) 1-(4-cyanophenyl)-4-[N-benzyl-N-[trans-4-(methoxycarbonyl)-cyclohexyl]-aminocarbonyl]-piperidine (2) 1-(4-cyanophenyl)-4-[N-[trans-4-(methoxycarbonyl)-cyclohexyl]-N-(2-phenylethyl)-aminocarbonyl]-piperidine (3) 1-(4-cyanophenyl)-4-[N-[trans-4-(methoxycarbonyl)-cyclohexyl]-N-(n-pentyl)-aminocarbonyl]-piperidine

EXAMPLE XXVII

1-[2-[4-(N-tert.Butyloxycarbonyl)-piperidino]-ethyl]-4-methoxycarbonyl-piperidine An equivalent mixture of N-tert.butyloxycarbonyl-4-(2-mesyloxy-ethyl)-piperidine, methyl piperidinocarboxylate with triethylamine is heated in dimethylformamide to 130° C. for 24 hours. After cooling the solvent is removed under reduced pressure and the residue is taken up in methylene chloride and washed with water. After drying over sodium sulphate and evaporating down, the residue is chromatographed over silica gel using methyl chloride/methanol as eluant. The crude product is used for the next stage of synthesis without any further purification.

EXAMPLE XXVIII

4-Methoxycarbonyl-1-[2-(4-piperidino)-ethyl]-piperidine

The crude 1-[2-(4-(N-tert.butyloxycarbonyl)-piperidino)-ethyl]-4-methoxycarbonyl-piperidine obtained above is dissolved in a (1:1) mixture of methylene chloride/trifluoroacetic acid and left to stand for 2 hours at ambient temperature. It is then evaporated to dryness in vacuo and the residue is distributed between methylene chloride and saturated aqueous sodium bicarbonate solution. The organic phase is separated off, dried over sodium Sulphate and evaporated to dryness in vacuo.

The following compound is obtained analogously to Example XXVIII:

(1) 4-amino-1- (4-cyanophenyl) -piperidine

EXAMPLE XXIX 1-(4-Cyanophenyl)-4-[2-(4-methoxycarbonyl-piperidino)-ethyl]-piperidine An equimolar solution of 4-methoxycarbonyl-1-[2-(4-piperidino)-ethyl]-piperidine, 4-fluorobenzonitrile and N-ethyl-diisopropylamine is heated to 140° C. for 4 hours. After cooling, it is chromatographed over silica gel using methylene chloride/methanol as eluant. After the solvent has been removed in vacuo, the residue remaining is triturated with petroleum ether and suction filtered.

Preparation of the end products:

EXAMPLE 1

1-(4-Amidinophenyl)-4-[N-[trans-4-(methoxycarbonyl)-cyclohexyl]-aminocarbonyl]-piperazine-hydrochloride At ambient temperature, dry hydrogen chloride is passed through a solution of 16.1 g of 1-(4-cyanophenyl)-4-[N-[trans-4-(methoxycarbonyl)-cyclohexyl]-aminocarbonyl]-piperazine in 250 ml of absolute methanol for 1.5 hours. The mixture is stirred for 3 hours at ambient temperature and the solvent is removed under reduced pressure at a bath temperature of 25°–35° C. The residue is dissolved in 250 ml of methanol. 50 g of ammonium carbonate are slowly added to the solution, with thorough stirring, and the mixture is stirred for 16 hours at ambient temperature. The solvent is removed under reduced pressure and the crude product is triturated with 200 ml of water and suction filtered. Then the solid material is triturated with 300 ml of hot acetone and suction filtered again. Yield: 14.1 g (77% of theory), $R_f$ value: 0.21 (silica gel; methylene chloride/methanol/conc. ammonia=4:1:0.25)

Mass spectrum: $(M+H)^+ = 388$

The following compounds are obtained analogously to Example 1:

(1) 1-(4-amidinophenyl)-4-[N-[trans-4-(methoxycarbonyl)-cyclohexyl]-N-methyl-aminocarbonyl]-piperazine-hydrochloride The crude product is chromatographed over silica gel. $R_f$ value: 0.27 (silica gel; methylene chloride/methanol/conc. ammonia=4:1:0.25)

Mass spectrum: M+ =401

(2) 1-(5-amidinopyrid-2-yl)-4-[N-[trans-4-(methoxycarbonyl)-cyclohexyl]-aminocarbonyl]-piperazine-hydrochloride $R_f$ value: 0.21 (silica gel; methylene chloride/methanol/conc. ammonia=4:1:0.25)

Mass spectrum: M+ =388

(3) 1-(5-amidinopyrid-2-yl)-4-[N-[trans-4-(methoxycarbonyl)-cyclohexyl]-aminocarbonyl]-piperazine-hydrochloride $R_f$ value: 0.15 (silica gel; methylene chloride/methanol/conc. ammonia=4:1:0.25)

Mass spectrum: M+ =387

(4) 1-(5-cyanopyrid-2-yl)-4-[4-(methoxycarbonylmethyl)-piperidinocarbonyl]-piperidine-hydrochloride The water-soluble crude product is triturated with methylene chloride/methanol and the suspension is filtered over silica gel. The filtrate is evaporated down under reduced pressure. The residue is triturated with acetone and suction filtered. $R_f$ value: 0.48 (silica gel; methylene chloride/methanol/conc. ammonia=9:1:0.1)

Mass spectrum: M+ =387

(5) 4-(4-amidinophenyl)-1-[N-[trans-4-(methoxycarbonyl)-cyclohexyl]-aminocarbonyl]-piperidine-hydrochloride The crude product is chromatographed over silica gel. Melting point: sintering from 176° C. $R_f$ value: 0.15 (silica gel; methylene chloride/methanol/conc. ammonia=4:1:0.25)

Mass spectrum: (M+1)+ =387

(6) 4-(4-amidinophenyl)-1-[4-(methoxycarbonylmethyl)-piperidinocarbonyl]-piperidine-hydrochloride The crude product is chromatographed over silica gel. Melting point: sintering from 205° C. $R_f$ value: 0.20 (silica gel; methylene chloride/methanol/conc. ammonia=4:1:0.25)

Mass spectrum: M+ =386

(7) 1-(4-amidinophenyl)-4-[N-[cis-4-(methoxycarbonyl)-cyclohexyl]-N-methyl-aminocarbonyl]-piperazine-hydrochloride The crude product is chromatographed over silica gel. $R_f$ value: 0.27 (silica gel; methylene chloride/methanol/conc. ammonia=4:1:0.25)

Mass spectrum: M+ =401

(8) 1-(4-amidinophenyl)-4-[N-benzyl-N-[trans-4-(methoxycarbonyl)-cyclohexyl]-aminocarbonyl]-piperazine-hydrochloride The crude product is chromatographed over silica gel. $R_f$ value: 0,26 (silica gel; methylene chloride/methanol/conc. ammonia=4:1:0.25)

Mass spectrum: M+ =477

(9) 1-(5-amidinopyrid-2-yl)-4-[N-[trans-4-(methoxycarbonyl)-cyclohexyl]-N-methyl-aminocarbonyl]-piperazine-hydrochloride $R_f$ value: 0.45 (Reversed Phase Plate RP18; methanol/5% saline solution=6:4)

Mass spectrum: M+ =402

(10) 4-(4-amidinophenyl)-1-[N-[trans- 4-(methoxycarbonyl)-cyclohexyl]-N-methyl-aminocarbonyl]-piperidine-hydrochloride $R_f$ value: 0.33 (silica gel; methylene chloride/methanol/conc. ammonia=4:1:0.25)

Mass spectrum: (M+H)+ =401

(11) 1-(5-amidinopyrid-2-yl)-4-[N-benzyl-N-[trans-4-(methoxycarbonyl)-cyclohexyl]-aminocarbonyl]-piperazine-hydrochloride

(12) 1-(4-amidinophenyl)-4-[4-(methoxycarbonylmethyl)-piperidinocarbonyl]-piperidine-hydrochloride Melting point: 228°–232° C. (decomp.)

(13) 1-(4-amidinophenyl)-4-[N-(3-methoxycarbonylpropyl)-aminocarbonyl]-piperidine-dihydrochloride

(14) 1-(4-amidinophenyl)-4-[N-(3-methoxycarbonylpropyl)-N-methyl-aminocarbonyl]-piperidine-hydrochloride

(15) 1-(4-amidinophenyl)-4-[N-benzyl-N-(3-methoxycarbonylpropyl)-aminocarbonyl]-piperidine-hydrochloride

(16) 1-(4-amidinophenyl)-4-[N-(3-methoxycarbonylpropyl)-N-(2-phenylethyl)-aminocarbonyl]-piperidine-hydrochloride

(17) 1-(4-amidinophenyl)-4-[N-(3-methoxycarbonylpropyl)-N-(3-phenylpropyl)-aminocarbonyl]-piperidine-hydrochloride

(18) 1-(4-amidinophenyl)-4-[N-(3-methoxycarbonylpropyl)-N-(n-pentyl)-aminocarbonyl]-piperidine-hydrochloride

(19) 1-(4-amidinophenyl)-4-[ 4-(methoxycarbonylmethylidene)-piperidinocarbonyl]-piperidine-hydrochloride

(20) 1-[4-amidinophenyl]-4-[4-(methoxycarbonylmethyl)-3,4-dehydro-piperidinocarbonyl]-piperidine-hydrochloride Melting point: 217°–220° C. (decomp.)

(21) 1-(4-amidinophenyl)-4-[N-(2-methoxycarbonylethyl)-aminocarbonylmethyl]-piperidine-hydrochloride Melting point: 240°–242° C. (decomp.)

(22) 1-(4-amidinophenyl)-4-[N-(2-methoxycarbonylethyl)-N-methyl-aminocarbonylmethyl]-piperidine-hydrochloride

(23) 1-(4-amidinophenyl)-4-[N-(2-methoxycarbonylethyl)-N-(2-phenylethyl)-aminocarbonylmethyl]-piperidine-hydrochloride

(24) 1-(4-amidinophenyl)-4-[N-[trans-4-(methoxycarbonyl)-cyclohexyl]-aminocarbonyl]-piperidine-hydrochloride

(25) 1-(4-amidinophenyl)-4-[4-(methoxycarbonylmethyl)-piperidinocarbonyl]-piperazine-hydrochloride Melting point: 248°–251° C. (decomp.)

(26) 1-(4-amidinophenyl)-4-[4-(methoxycarbonylmethylidene)-piperidinocarbonyl]-piperazine-hydrochloride

(27) 1-(4-amidinophenyl)-4-[4-(methoxycarbonylmethyl)-3,4-dehydro-piperidinocarbonyl]-piperazine-hydrochloride Melting point: 228°–230° C. (decomp.)

(28) 1-(4-amidinophenyl)-4-[N-(2-methoxycarbonylethyl)-aminocarbonylmethyl]-piperazine-hydrochloride Melting point: 228°–230° C. (decomp.)

(29) 1-(4-amidinophenyl)-4-[N-(2-methoxycarbonylethyl)-N-(2-phenylethyl)-aminocarbonylmethyl]-piperazine-hydrochloride

(30) 1-(5-amidinopyrid-2-yl)-4-[N-[trans-4-(methoxycarbonyl)-cyclohexyl]-N-[(morpholinocarbonyl)-methyl]-aminocarbonyl]-piperazine-hydrochloride

(31) 4-(4-amidinophenyl)-1-[N-benzyl-N-[trans-4-(methoxycarbonyl)-cyclohexyl]-aminocarbonyl]-piperidine-hydrochloride

(32) 4-(4-amidinophenyl)-1-[N-[trans-4-(methoxycarbonyl)-cyclohexyl]-N-[(morpholinocarbonyl)methyl]-aminocarbonyl]-piperidine-hydrochloride

(33) 1-(4-amidinophenyl)-4-[N-[4-(methoxycarbonyl)-butyl]-aminocarbonyl]-piperazine-hydrochloride

(34) 4-(4-amidinophenyl)-1-[N-[4-(methoxycarbonyl)-butyl]-N-methyl-aminocarbonyl]-piperidine-hydrochloride

(35) 1-(5-amidinopyrid-2-yl)-4-[N-[3-(methoxycarbonyl)-propyl]-aminocarbonyl]-piperidine-hydrochloride

(36) 1-(4-amidinophenyl)-4-[N-benzyl-N-[trans-4-(methoxycarbonyl)-cyclohexyl]-aminocarbonyl]-piperidine-hydrochloride

(37) 1-(4-amidinophenyl)-4-[N-[trans-4-(methoxycarbonyl)-cyclohexyl]-N-(2-phenylethyl)-aminocarbonyl]-piperidine-hydrochloride Melting point: 288°–290° C. (decomp.)

(38) 1-(4-amidinophenyl)-4-[N-[trans-4-(methoxycarbonyl)-cyclohexyl]-N-(3-phenylpropyl)-aminocarbonyl]-piperidine-hydrochloride Melting point: 242°–245° C. (decomp.)

(39) 1-(4-amidinophenyl)-4-[N-[trans-4-(methoxycarbonyl)-cyclohexyl]-N-(n-pentyl)aminocarbonyl]-piperidine-hydrochloride Melting point: 270°–272° C. (decomp.)

(40) 1-(4-amidinophenyl)-4-[4-(methoxycarbonylmethyl)piperidinomethyl]-piperidine-dihydrochloride Amorphous substance Mass spectrum: $(M+H)^+ = 373$

(41) 1-(4-amidinophenyl)-4-[N-[trans-4-(methoxycarbonyl)-cyclohexyl]-aminomethyl]-piperidine-dihydrochloride

(42) 1-(4-amidinophenyl)-4-[N-[trans-4-(methoxycarbonyl)-cyclohexyl]-N-methyl-aminomethyl]-piperidine-dihydrochloride

(43) 1-(4-amidinophenyl)-4-[4-(methoxycarbonylmethylidene)-piperidinomethyl]-piperidine-dihydrochloride

(44) 4-(4-amidinophenyl)-1-[N-[trans-4-(methoxycarbonyl)-cyclohexyl]-aminocarbonyl]-3,4-dehydro-piperidine-hydrochloride

(45) 4-(4-amidinophenyl)-1-[N-benzyl-N-[trans-4-(methoxycarbonyl)-cyclohexyl]-aminocarbonyl]-3,4-dehydro-piperidine-hydrochloride

(46) 1-(4-amidinophenyl)-4-[N-[trans-4-(methoxycarbonyl)-cyclohexyl]-aminocarbonyl]-2-piperidone-hydrochloride

(47) 1-(4-amidinophenyl)-4-[N-benzyl-N-[trans-4-(methoxycarbonyl)-cyclohexyl]-aminocarbonyl]-2-piperidone-hydrochloride

(48) 1-(5-amidinopyrimid-2-yl)-4-[N-[trans-4-(methoxycarbonyl)-cyclohexyl]-aminocarbonyl]-piperidine-hydrochloride

(49) 1-(4-amidino-2-methylphenyl)-4-[N-[trans-4-(methoxycarbonyl)-cyclohexyl]-aminocarbonyl]-piperazine-hydrochloride

(50) 1-(5-amidinopyrid-2-yl)-4-[4-(methoxycarbonylmethyl)-piperazinocarbonyl]-piperidine-hydrochloride

(51) 1-(4-amidinophenyl)-4-[2-[N-[2-(methoxycarbonyl)-ethyl]-amino]-ethyl]-piperidine-hydrochloride

(52) 1-(4-amidinophenyl)-4-[2-[4-(methoxycarbonyl)-piperdino]-ethyl]-piperidine-hydrochloride

(53) 1-(4-amidinophenyl)-4-[2-(4-methoxycarbonyl-piperidino)-ethyl]-piperidine

(54) 1-(4-amidinophenyl)-4-[(3-methoxycarbonyl-propyl)-carbonylamino]-piperidine

(55) 1-(4-amidinophenyl)-4-[(4-trans-methoxycarbonyl-cyclohexyl)-carbonylamino]-piperidine

(56) 1-(4-amidinophenyl)-4-[(4-trans-methoxycarbonyl-cyclohexyl)-carbonylmethylamino]-piperidine

EXAMPLE 2

1-(4-Amidinophenyl)-4-[N-[trans-4-carboxycyclohexyl]aminocarbonyl]-piperazine-dihydrochloride-hydrate A solution of 4.0 g of 1-(4-amidinophenyl)-4-[N-[trans-4-(methoxycarbonyl)-cyclohexyl]-aminocarbonyl]-piperazine-hydrochloride in 50 ml of semi-concentrated hydrochloric acid is stirred at ambient temperature for 5 hours. The solvent is removed under reduced pressure, the crude product is triturated with acetone, suction filtered and dried. Yield: 4.2 g (96% of theory), $R_f$ value: 0.15 (silica gel; methylene chloride/methanol/conc. ammonia = 2:1:0.25)

|  | C | H | N |
|---|---|---|---|
| Calc. × 2 HCl × 1 H$_2$O: | 49.14 | 6.73 | 15.08 |
| Found: | 49.49 | 6.86 | 14.78 |

Mass spectrum: $(M+H)^+ = 374$

The following compounds are obtained analogously to Example 2:

(1) 1-(4-amidinophenyl)-4-[N-(trans-4-carboxycyclohexyl)-N-methyl-aminocarbonyl]-piperazine-dihydrochloride The reaction solution is stirred for 16 hours at ambient temperature. $R_f$ value: 0.30 (silica gel; methylene chloride/methanol/conc. ammonia = 2:1:0.25)

Mass spectrum: $(M+H)^+ = 388$ (2) 1-(5-amidinopyrid-2-yl)-4-[N-(trans-4-carboxycyclohexyl)-aminocarbonyl]-piperidine-dihydrochloride $R_f$ value: 0.63 (Reversed Phase Plate RP18; methanol/5% saline solution = 6:4)

Mass spectrum: $(M+H)^+ = 374$ (3) 4-(4-amidinophenyl)-1-[N-(trans-4-carboxycyclohexyl)-aminocarbonyl]-piperidine-hydrochloride The product crystallises out. Melting point: sintering from 252° C. $R_f$ value: 0.13 (silica gel; methylene chloride/methanol/conc. ammonia = 2:1:0.25)

Mass spectrum: $(M+H)^+ = 373$ (4) 4-(4-amidinophenyl)-1-[4-(carboxymethyl)-piperidinocarbonyl]-piperidine-hydrochloride $R_f$ value: 0.35 (silica gel; methylene chloride/methanol/conc. ammonia = 2:1:0.25)

Mass spectrum: $(M+H)^+ = 373$ (5) 1-(4-amidinophenyl)-4-[N-(cis-4-carboxycyclohexyl)-N-methyl-aminocarbonyl]-piperazine-dihydrochloride $R_f$ value: 0.50 (silica gel; methylene chloride/methanol/conc. ammonia = 2:1:0.25)

Mass spectrum: $(M+H)^+ = 388$ (6) 1-(4-amidinophenyl)-4-[N-benzyl-N-(trans-4-carboxycyclohexyl)-aminocarbonyl]-piperazine-dihydrochloride $R_f$ value: 0.47 (silica gel; methylene chloride/methanol/conc. ammonia = 2:1:0.25)

Mass spectrum: $(M+H)^+ = 464$ (7) 1-(5-amidinopyrid-2-yl)-4-[N-(trans-4-carboxycyclohexyl)-aminocarbonyl]-piperazine-dihydrochloride Melting point: sintering from 180° C. $R_f$ value: 0.18 (silica gel; methylene chloride/methanol/conc. ammonia = 2:1:0.25)

Mass spectrum: $(M+H)^+ = 375$ (8) 1-(5-amidinopyrid-2-yl)-4-[N-(trans-4-carboxycyclohexyl)-N-methyl-aminocarbonyl]-piperazine-dihydrochloride $R_f$ value: 0.63 (Reversed Phase Plate RP18; methanol/5% saline solution = 6:4)

Mass spectrum: $(M+H)^+ = 389$ (9) 1-(5-amidinopyrid-2-yl)-4-[N-benzyl-N-(trans-4-carboxycyclohexyl)-aminocarbonyl]-piperazine-dihydrochloride

(10) 1-(5-aminomethylpyrid-2-yl)-4-[4-(carboxymethyl)-piperidinocarbonyl]-piperidine-dihydrochloride $R_f$ value: 0.09 (silica gel; methylene chloride/methanol/conc. ammonia = 4:1:0.25)

Mass spectrum: M+ =360

(11) 4-(4-aminomethylphenyl)-1-[N-(trans-4-carboxycyclohexyl)-aminocarbonyl]-piperidine-hydrochloride The mixture is stirred for 20 hours at ambient temperature. The crude product is triturated with a little methanol and suction filtered. Melting point: sintering from 243° C. $R_f$ value: 0.13 (silica gel; methylene chloride/methanol/conc. ammonia=4:1:0.25)

Mass spectrum: $(M-H)^- = 358$

(12) 4-(4-aminomethylphenyl)-1-[ 4-(carboxymethyl)-piperidinocarbonyl]-piperidine-hydrochloride $R_f$ value: 0.19 (silica gel; methylene chloride/methanol/conc. ammonia=4:1:0.25)

Mass spectrum: $(M+H)^+ = 360$

(13) 1-(4-aminomethylphenyl)-4-[4-(carboxymethyl)-piperidinocarbonyl]-piperidine-dihydrochloride

(14) 1-(4-amidinophenyl)-4-[4-(carboxymethylidene)-piperidinocarbonyl]-piperidine-dihydrochloride

(15) 1-(4-amidinophenyl)-4-[4-(carboxymethyl )-3,4-dehydro-piperidinocarbonyl]-piperidine-dihydrochloride

(16) 1-(4-aminomethylphenyl)-4-[4-(carboxymethylidene)-piperidinocarbonyl]-piperidine-dihydrochloride

(17) 1-(4-amidinophenyl)-4-[4-(carboxymethyl)-piperidinocarbonyl]-piperazine-dihydrochloride Melting point: 190°-192° C. (decomp.)

(18) 1-(4-amidinophenyl)-4-[4-(carboxymethylidene)-piperidinocarbonyl]-piperazine-dihydrochloride

(19) 1-(4-amidinophenyl)-4-[4-(carboxymethyl)-3,4-dehydro-piperidinocarbonyl]-piperazine-dihydrochloride Melting point: 175°-180° C. (decomp.)

(20) 1-(4-amidinophenyl)-4-[N-(2-carboxyethyl)-N-(2-phenylethyl)-aminocarbonylmethyl]-piperazine

(21) 1-(5-amidinopyrid-2-yl)-4-[N-(trans-4-carboxycyclohexyl)-N-[(morpholinocarbonyl)-methyl]-aminocarbonyl]-piperazine-dihydrochloride

(22) 1-(5-aminomethylpyrid-2-yl)-4-[N-(trans- 4-carboxycyclohexyl)-aminocarbonyl]-piperazine-dihydrochloride Melting point: sintering from 203° C. $R_f$ value: 0.17 (silica gel; methylene chloride/methanol/conc. ammonia=4:1:0.25)

Mass spectrum: $(M+H)^+ = 362$

(23) 4-(4-amidinophenyl)-1-[N-benzyl-N-(trans-4-carboxycyclohexyl)-aminocarbonyl]-piperidine-hydrochloride

(24) 4-(4-amidinophenyl)-1-[N-(trans-4-carboxycyclohexyl)-N-[(morpholinocarbonyl)-methyl]-aminocarbonyl]-piperidine-hydrochloride

(25) 1-(4-amidinophenyl)-4-[N-(4-carboxybutyl)-aminocarbonyl]-piperazine-dihydrochloride

(26) 4-(4-amidinophenyl)-1-[N-(4-carboxybutyl)-N-methylaminocarbonyl]-piperidine-hydrochloride

(27) 1-(5-amidinopyrid-2-yl)-4-[N-(3-carboxypropyl)-aminocarbonyl]-piperidine-dihydrochloride

(28) 1-(4-amidinophenyl)-4-[N-(trans-4-carboxycyclohexyl)-aminomethyl]-piperidine-trihydrochloride

(29) 1-(4-aminomethylphenyl)-4-[N-(trans-4-carboxycyclohexyl)-aminomethyl]-piperidine-trihydrochloride

(30) 1-(4-amidinophenyl)-4-[N-(trans-4-carboxycyclohexyl)-N-methyl-aminomethyl]-piperidine-trihydrochloride

(31) 1-(4-aminomethylphenyl)-4-[N-(trans-4-carboxycyclohexyl)-N-methyl-aminomethyl]-piperidine-trihydrochloride

(32) 1-(4-aminomethylphenyl)-4-[4-(carboxymethyl)-piperidinomethyl]-piperidine-trihydrochloride

(33) 4-(4-amidinophenyl)-1-[N-(trans-4-carboxycyclohexyl)-aminocarbonyl]-3,4-dehydro-piperidine-hydrochloride

(34) 4-(4-amidinophenyl)-1-[N-benzyl-N-(trans-4-carboxycyclohexyl)-aminocarbonyl]-3,4-dehydro-piperidine-hydrochloride

(35) 1-(4-amidinophenyl)-4-[N-(trans-4-carboxycyclohexyl)-aminocarbonyl]-2-piperidone-hydrochloride

(36) 1-( 4-amidinophenyl ) -4-[N-benzyl-N-(trans-4-carboxycyclohexyl)-aminocarbonyl]-2-piperidone-hydrochloride

(37) 1-(5-amidinopyrimid-2-yl)-4-[N-(trans-4-carboxycyclohexyl)-aminocarbonyl]-piperidine-dihydrochloride

(38) 1-(4-amidino-2-methylphenyl)-4-[N-(trans-4-carboxycyclohexyl)-aminocarbonyl]-piperazine-dihydrochloride

(39) 1-(5-amidinopyrid-2-yl)-4-[4-(carboxymethyl)-piperazino-carbonyl]-piperidine-trihydrochloride

(40) 1-(4-amidinophenyl)-4-[2-[(2-carboxyethyl)-amino]-ethyl]-piperidine-trihydrochloride

(41) 1-(4-amidinophenyl)-4-[2-[4-carboxypiperidino]-ethyl]-piperidine-trihydrochloride

(42) 1-(5-amidinopyrid-2-yl )-4-[4-(carboxymethyl)-piperidinocarbonyl]-piperidine-dihydrochloride $R_f$ value: 0.12 (silica gel; methylene chloride/methanol/conc. ammonia=2:1:0.25)

Mass spectrum: $(M+H)^+ = 374$

(43) 1-(4-amidinophenyl)-4-[4-(carboxymethyl)-piperidinomethyl]-piperidine-hydrochloride Melting point: 255°-257° C.

(44) 1-(4-amidinophenyl)-4-[2-(4-carboxypiperidino)-ethyl]-piperidine

(45) 1-(4-amidinophenyl)-4-[(3-carboxypropyl)-carbonyl-amino]-piperidine

(46) 1-(4-amidinophenyl)-4-[(4-trans-carboxycyclohexyl)-carbonylamino]-piperidine

(47) 1-(4-amidinophenyl)-4-[(4-trans-carboxycyclohexyl)-carbonylmethylamino]-piperidine

EXAMPLE 3

1-(4-Aminomethylphenyl)-4-[N-(trans-4-carboxycyclohexyl)-aminocarbonyl]-piperazine 400 mg of 1-(4-aminomethylphenyl)-4-[N-[trans-4-(methoxycarbonyl)-cyclohexyl]-aminocarbonyl]-piperazine-hydrochloride and 3 ml of a 1.4 molar aqueous lithium hydroxide solution in 3 ml of tetrahydrofuran and 2 ml of water is stirred at ambient temperature for 2 hours. Then 3.2 ml of 1N hydrochloric acid are added dropwise and some of the solvent is evaporated off under reduced pressure. The precipitate is suction filtered, triturated with acetone, suction filtered again and dried. Yield: 330 mg (94% of theory), $R_f$ value: 0.47 (silica gel; methylene chloride/methanol/conc. ammonia=2:1:0.25) Mass spectrum: M+ =360

The following compounds are obtained analogously to Example 3:

(1) 1-[4-(N-benzyloxycarbonyl-amidino)-phenyl]-4-[N-(trans-4-carboxycyclohexyl)-aminocarbonyl]-piperazine $R_f$ value: 0.41 (silica gel; methylene chloride/methanol/conc. ammonia=4:1:0.25)

Mass spectrum: $(M+H)^+ = 508$ (2) 4-(4-amidinophenyl)-1-[N-(trans-4-carboxycyclohexyl)-aminocarbonyl]-piperidine $R_f$ value: 0.42 (silica gel; methylene chloride/methanol/conc. ammonia=2:1:0.25)

(3) 1-(4-aminomethylphenyl)-4-[N-(trans-4-carboxycyclo-hexyl)-N-methyl-aminocarbonyl]-piperazine (4) 1-(4-amidinophenyl)-4-[4-(carboxymethyl)-piperidino-carbonyl]-piperidine
Melting point: 305°–308° C. (decomp.)

(5) 1-[4-(N-benzyloxycarbonyl-amidino)-phenyl]-4-[4-(carboxymethyl)-piperidinocarbonyl]-piperidine (6) 1-(4-amidinophenyl)-4-[N-(3-carboxypropyl)-amino-carbonyl]-piperidine (7) 1-(4-amidinophenyl)-4-[(3-carboxypropyl)-methylamino-carbonyl]-piperidine (8) 1-(4-amidinophenyl)-4-[N-benzyl-N-(3-carboxypropyl)aminocarbonyl]-piperidine (9) 1-(4-amidinophenyl)-4-[N-(3-carboxypropyl)-N-(2-phenylethyl) -aminocarbonyl]-piperidine

(10) 1-(4-amidinophenyl)-4-[N-(3-carboxypropyl)-N-(3-phenylpropyl)-aminocarbonyl]-piperidine

(11) 1-(4-amidinophenyl)-4-[N-(3-carboxypropyl)-N-(n-pentyl)-aminocarbonyl]-piperidine

(12) 1-(4-amidinophenyl) -4-[N-(2-carboxyethyl)-amino-carbonylmethyl]-piperidine

(13) 1-(4-aminomethylphenyl)-4-[N-(2-carboxyethyl)-N-methyl-aminocarbonylmethyl]-piperidine

(14) 1-(4-amidinophenyl) -4-[N-(2-carboxyethyl)-N-(2-phenylethyl)-aminocarbonylmethyl]-piperidine

(15) 1-(4-amidinophenyl)-4-[N-(trans-4-carboxycyclo-hexyl)-aminocarbonyl]-piperidine

(16) 1-(4-amidinophenyl)-4-[N-(trans-4-carboxycyclo-hexyl)-N-methyl-aminocarbonyl]-piperidine

(17) 1-(4-aminomethylphenyl)-4-[N-(trans-4-carboxycyclo-hexyl)-aminocarbonyl]-piperidine-hydrochloride Melting point: 272°–274° C. (decomp.)

(18) 1-(4-aminomethylphenyl)-4-[4-(carboxymethyl)-piperidinocarbonyl]-piperazine

(19) 1-[4-(N-allyloxycarbonyl-amidino)-phenyl]-4-[4-(carboxymethyl)-piperidinocarbonyl]-piperazine

(20) 1-(4-amidinophenyl)-4-[N-(2-carboxyethyl)-amino-carbonylmethyl]-piperazine Melting point: 282°–286° C. (decomp.)

(21) 4-[4-(N-benzyloxycarbonyl-amidino)-phenyl]-1-[N-(trans-4-carboxycyclohexyl)-aminocarbonyl]-piperidine

(22) 1-(4-amidinophenyl)-4-[4-(carboxymethylidene)-piperidinomethyl]-piperidine

(23) 1-(4-amidinophenyl)-4-[N-benzyl-N-(trans-4-carboxy-cyclohexyl)-aminocarbonyl]-piperidine

(24) 1-(4-amidinophenyl)-4-[N-(trans-4-carboxycyclohexyl)-N-(2-phenylethyl)-aminocarbonyl]-piperidine Melting point: 186°–190° C. (decomp.)

(25) 1-(4-amidinophenyl)-4-[N-(trans-4-carboxycyclohexyl)-N-(3-phenylpropyl)-aminocarbonyl]-piperidine $R_f$ value: 0.66 (silica gel; methylene chloride/methanol=4:1)

(26) 1-(4-amidinophenyl)-4-[N-(trans-4-carboxycyclohexyl)-N-(n-pentyl)-aminocarbonyl]-piperidine Mass spectrum: (M+H)+ =443

EXAMPLE 4

1-(4-Aminomethylphenyl)-4-[N-[trans-4-(methoxycarbonyl)-cyclohexyl]-aminocarbonyl]-piperazine-hydrochloride A solution of 1.0 g of 1-(4-cyanophenyl)-4-[N-[trans-4-(meth-oxycarbonyl)-cyclohexyl]-aminocarbonyl]-pip erazine in 100 ml of methanol and 15 ml of ethereal hydrochloric acid is hydrogenated for 3 hours at ambient temperature in the presence of 200 mg of 10% palladium on charcoal under a hydrogen pressure of 3 bar. Then, the catalyst is filtered off and the filtrate is evaporated to dryness under reduced pressure. The crude product is dissolved in methanol and then mixed with ether. The precipitate is suction filtered and dried. Yield: 790 mg (71% of theory), $R_f$ value: 0.62 (silica gel; methylene chloride/methanol/conc. ammonia=2:1:0.25)

Mass spectrum: M+ =374

The following compounds are obtained analogously to Example 4:

(1) 1-(4-aminomethylphenyl)-4-[N-[trans-4-(methoxycarbonyl)-cyclohexyl]-N-methyl-aminocarbonyl]-piperazine-hydrochloride (2) 1-(5-aminomethylpyrid-2-yl)-4-[4-[(methoxycarbonyl)-methyl]-piperidinocarbonyl]-piperidine-dihydrochloride The hydrogenation is carried out in methanol/methanolic hydrochloric acid (1:1). The crude product is chromatographed over silica gel. The product is dissolved in methanolic hydrochloric acid, the solvent is evaporated off under reduced pressure, the residue is triturated with ether and suction filtered. $R_f$ value: 0.67 (silica gel; methylene chloride/methanol/-conc. ammonia=4:1:0.25)

Mass spectrum: M+ =374

(3) 4-(4-aminomethylphenyl)-1-[N-[trans-4-(methoxycarbonyl)-cyclohexyl]-aminocarbonyl]-piperidine-hydrochloride The crude product is triturated with a little methanol and suction filtered. Melting point: 238°–242° C. $R_f$ value: 0.44 (silica gel; methylene chloride/methanol/conc. ammonia=9:1:0.1)

Mass spectrum: M+ =373

(4) 4-(4-aminomethylphenyl)-1-[4-[(methoxycarbonyl)-methyl]-piperidinocarbonyl]-piperidine-hydrochloride The hydrogenation is carried out in methanol/methanolic hydrochloric acid (1:1). The crude product is obtained in crystalline form. Melting point: Sintering from 190° C. $R_f$ value: 0.44 (silica gel; methylene chloride/methanol/conc. ammonia=9:1:0.1)

Mass spectrum: M+ =373

(5) 1-(4-aminomethylphenyl)-4-[4-[(methoxycarbonyl)-methyl]-piperidinocarbonyl]-piperidine-dihydrochloride (6) 1-(4-aminomethylphenyl)-4-[N-(3-carboxypropyl)-aminocarbonyl]-piperidine-dihydrochloride (7) 1-(4-aminomethylphenyl)-4-[4-[(methoxycarbonyl)-methyl]-piperidinocarbonyl]-piperidine-dihydrochloride (8) 1-(4-aminomethylphenyl)-4-[N-[2-(methoxycarbonyl)-ethyl]-N-methyl-aminocarbonylmethyl]-piperidine-dihydrochloride (9) 1-(4-aminomethylphenyl)-4-[N-[trans-4-(methoxycarbonyl)-cyclohexyl]-aminocarbonyl]-piperidine-dihydrochloride Melting point: 215°–218° C. (decomp.)

(10) 1-(4-aminomethylphenyl)-4-[4-(methoxycarbonyl-methyl)-piperidinocarbonyl]-piperazine-dihydrochloride

(11) 1-(5-aminomethylpyrid-2-yl)-4-[N-[trans-4-(methoxy-carbonyl)-cyclohexyl]-aminocarbonyl]-piperazine-dihydrochloride The crude product is chromatographed over silica gel. $R_f$ value: 0.70 (silica gel; methylene chloride/methanol/conc. ammonia=4:1:0.25)

Mass spectrum: M+ =375

(12) 1-(4-aminomethylphenyl)-4-[4-(methoxycarbonyl-methyl)-piperidinomethyl]-piperidine-trihydrochloride

(13) 1-(4-aminomethylphenyl)-4-[N-[trans-4-(methoxy-carbonyl)-cyclohexyl]-aminomethyl]-piperidine-trihydrochloride

(14) 1-(4-aminomethylphenyl)-4-[N-[trans-4-(methoxy-carbonyl)-cyclohexyl]-N-methyl-aminomethyl]-piperidine-trihydrochloride

EXAMPLE 5

1-[4-(N-Methoxycarbonyl-amidino)-phenyl]-4-[N-[trans-4-(methoxycarbonyl)-cyclohexyl]-aminocarbonyl]-piperazine To a suspension of 0.50 g of 1-(4-amidinophenyl)-4-[N-[trans-4-(methoxycarbonyl)-cyclohexyl]-aminocarbonyl]-piperazine-hydrochloride in 30 ml methylene chloride are added dropwise 2.5 ml of 1N sodium hydroxide solution followed by 0.10 ml of methyl chloroformate. The mixture is stirred for 40 minutes at ambient temperature. The solution is diluted with water and the aqueous phase is extrated with methylene chloride. The organic phase is washed with saturated saline solution and dried over sodium sulphate. The solvent is removed under reduced pressure and the residue is chromatographed over silica gel. Yield: 0.36 g (69% of theory), $R_f$ value: 0.32 (silica gel; methylene chloride/methanol=15:1)

Mass spectrum: $(M+H)^+ = 446$

The following compounds are obtained analogously to Example 5:

(1) 1-[4-(N-benzyloxycarbonyl-amidino)-phenyl]-4-[N-[trans-4-(methoxycarbonyl)-cyclohexyl]-aminocarbonyl]-piperazine To a suspension of 1-(4-amidinophenyl)-4-[N-[trans-4-(methoxycarbonyl)-cyclohexyl]-aminocarbonyl]-piperazine-hydrochloride and benzyl chloroformate in methylene chloride/water (5:1) 1N sodium hydroxide solution is added dropwise until the pH remains at 9. After 2 hours stirring at ambient temperature, the product is suction filtered. $R_f$ value: 0.86 (silica gel; methylene chloride/methanol/conc. ammonia=4: 1: 0.25)

Mass spectrum: $(M+H)^+ = 522$ (2) 1-[N-[trans-4-(methoxycarbonyl)-cyclohexyl]-amino-carbonyl]-4-[4-(N-ethoxycarbonyl-amidino)-phenyl]-piperazine Using ethyl chloroformate (3) 1-[4-(N-methoxycarbonyl-amidino)-phenyl]-4-[N-trans-4-(methoxycarbonyl)-cyclohexyl]-N-methyl-aminocarbonyl]-piperazine (4) 1-[N-[trans-4-(methoxycarbonyl)-cyclohexyl]-N-methyl-aminocarbony]-4-[4-(N-ethoxycarbonyl-amidino)-phenyl]-piperazine (5) 1-[4-(N-methoxycarbonyl-amidino)-phenyl]-4-[4-(methoxycarbonylmethyl)-piperidinocarbonyl]-piperidine Melting point: 175°-178° C.

(6) 1-[4-(N-benzyloxycarbonyl-amidino)-phenyl]-4-[4-(methoxycarbonylmethyl)-piperidinocarbonyl]-piperidine Using benzyl chloroformate (7) 1-[4-(N-acetoxymethoxycarbonyl-amidino)-phenyl]-4-[4-(methoxycarbonylmethyl)-piperidinocarbonyl]-piperidine Using acetyloxymethyl-(4-nitrophenyl carbonate) and N-ethyl-diisopropylamine (8) 1-[4-[N-(1-acetoxyethoxycarbonyl)-amidino]-phenyl]-4-[4-(methoxycarbonylmethyl)-piperidinocarbonyl]-piperidine Using 1-acetoxyethyl-(4-nitrophenyl carbonate) and N-ethyl-diisopropylamine (9) 1-[4-(N-methoxycarbonyl-amidino)-phenyl]-4-[N-(3-methoxycarbonylpropyl)-aminocarbonyl]-piperidine

(10) 1-[4-(N-methoxycarbonyl-amidino)-phenyl]-4-[N-(3-methoxycarbonylpropyl)-N-methyl-aminocarbonyl]-piperidine

(11) 1-[4-(N-benzyloxycarbonyl-amidino)-phenyl]-4-[4-(methoxycarbonylmethylidene)-piperidinocarbonyl]-piperidine Using benzyl chloroformate

(12) 1-[4-(N-methoxycarbonyl-amidino)-phenyl]-4-[4-(methoxycarbonylmethylidene)-piperidinocarbonyl]-piperidine

(13) 1-[4-(N-methoxycarbonyl-amidino)-phenyl]-4-[N-trans-4-(methoxycarbonyl)-cyclohexyl]-aminocarbonyl]-piperidine

(14) 1-[4-[N-(1-acetoxyethoxycarbonyl)-amidino]-phenyl]-4-[N-[trans-4-(methoxycarbonyl)-cyclohexyl]-N-methyl-aminocarbonyl]-piperidine Using 1-acetoxyethyl-(4-nitrophenylcarbonate) and ethyl-diisopropylamine

(15) 1-[4-(N-allyloxycarbonyl-amidino)-phenyl]-4-[4-(methoxycarbonylmethyl)-piperidinocarbonyl]-piperazine Using allyl chloroformate and N-ethyl-diisopropylamine

(16) 1-[4-(N-methoxycarbonyl-amidino)-phenyl]-4-[N-(2-methoxycarbonylethyl)-aminocarbonylmethyl]-piperazine

(17) 1-[4-(N-methoxycarbonyl-amidino)-phenyl]-4-[N-[trans-4-(isobutoxycarbonyl)-cyclohexyl]-aminocarbonyl]-piperazine

(18) 1-[4-(N-methoxycarbonyl-amidino)-phenyl]-4-[N-[trans-4-(isopropoxycarbonyl)-cyclohexyl]-aminocarbonyl]-piperazine

(19) 1-[4-(N-methoxycarbonyl-amidino)-phenyl]-4-[N-[trans-4-(isopropoxycarbonyl)-cyclohexyl]-N-methyl-aminocarbonyl]-piperazine

(20) 4-[4-(N-benzyloxycarbonyl-amidino)-phenyl]-1-[N-[trans-4-(methoxycarbonyl)-cyclohexyl]-aminocarbonyl]-piperidine Using benzyl chloroformate in methylene chloride/water (5:1) and 1N sodium hydroxide solution.

(21) 4-[4-(N-methoxycarbonyl-amidino)-phenyl]-1-[N-[trans-4-(methoxycarbonyl)-cyclohexyl]-aminocarbonyl]-piperidine

(22) 4-[4-(N-methoxycarbonyl-amidino)-phenyl]-1-[N-[trans-4-(isopropoxycarbonyl)-cyclohexyl]-aminocarbonyl]-piperidine

(23) 1-[N-benzyl-N-[trans-4-(methoxycarbonyl)-cyclo-hexyl]-aminocarbonyl]-4-[4-(N-methoxycarbonyl-amidino)-phenyl]-piperidine

(24) 1-[4-(N-methoxycarbonyl-amidino)-phenyl]-4-[4-(methoxycarbonyl)-piperidinomethyl]-piperidine

(25) 1-[4-(N-methoxycarbonyl-amidino)-phenyl]-4-[N-[trans-4-(methoxycarbonyl)-cyclohexyl]-aminocarbonyl]-piperidine

(26) 1-[4-(N-methoxycarbonyl-amidino)-phenyl]-4-[2-(4-methoxycarbonyl-piperidino)-ethyl]-piperidine

(27) 1-[4-(N-methoxycarbonyl-amidino)-phenyl]-4-[(3-methoxycarbonylpropyl)-carbonylamino]-piperidine

(28) 1-[4-(N-methoxycarbonyl-amidino)-phenyl]-4-[(4-trans-methoxycarbonyl-cyclohexyl)-carbonylamino]-piperidine

(29) 1-[4-(N-methoxycarbonyl-amidino)-phenyl]-4-[(4-trans-methoxycarbonyl-cyclohexyl)-carbonylmethylamino]-piperidine

EXAMPLE 6

1-[4-(N-Benzyloxycarbonyl-amidino)-phenyl]-4-[N-[trans-4-[(morpholinocarbonyl)-methoxycarbonyl]-cyclohexyl]-aminocarbonyl]-piperazine To a solution of 1.5 g of 1-[4-(N-benzyloxycarbonyl)-amidino)-phenyl-4-[N-(trans-4-carboxycyclohexyl)-aminocarbonyl]-piperazine and 1.0 g of chloroacetyl-morpholide in 40 ml dimethylsulfoxide are added 0.65 g of potassium hydrogen carbonate and 0.9 g of potassium carbonate and the mixture is stirred for two hours at ambient temperature. The reaction solution is diluted with water and the aqueous phase is extracted with methylene chloride. The organic phase is washed with saturated saline solution and filtered over activated charcoal and the filtrate is evaporated to dryness under reduced pressure. The residue remaining is triturated with ether and suction filtered. Yield: 1.3 g (69% of theory), R$_f$ value: 0.38 (silica gel; methylene chloride/methanol = 15:1)

Mass spectrum: (M+H)+ = 635

The following compounds are obtained analogously to Example 6:

(1) 1-[4-(N-benzyloxycarbonyl-amidino)-phenyl]-4-[N-[trans-4-[(dimethylaminocarbonyl)-methoxycarbonyl]-cyclohexyl]-aminocarbonyl]-piperazine α-Chloroacetic acid-dimethylamide is used. R$_f$ value: 0.40 (silica gel; methylene chloride/methanol = 15:1)

Mass spectrum: (M+H)+ = 593

(2) 1-[4-(N-benzyloxycarbonyl-amidino)-phenyl]-4-[N-[trans-4-[(piperidinocarbonyl)-methoxycarbonyl]-cyclohexyl]-aminocarbonyl]-piperazine α-Chloroacetic acid piperidide is used.

(3) 4-[4-(N-benzyloxycarbonyl-amidino)-phenyl]-1-[N-[trans-4-[(dimethylaminocarbonyl)-methoxycarbonyl]-cyclohexyl]-aminocarbonyl]-piperidine (4) 4-[4-(N-benzyloxycarbonyl-amidino)-phenyl]-1-[N-[trans-4-[(piperidinocarbonyl)-methoxycarbonyl]-cyclo-hexyl]-aminocarbonyl]-piperidine (5) 4-[4-(N-benzyloxycarbonyl-amidino)-phenyl]-1-[N-[trans-4-[(morpholinocarbonyl)-methoxycarbonyl]-cyclohexyl]-aminocarbonyl]-piperidine

EXAMPLE 7

1-(4-Amidinophenyl)-4-[N-[trans-4-(isopropoxycarbonyl)-cyclohexyl]-aminocarbonyl]-piperazine-dihydrochloride At 0° C., hydrogen chloride is passed through a suspension of 0.50 g of 1-(4-amidinophenyl)-4-[N-(trans-4-carboxycyclohexyl)-aminocarbonyl]-piperazine-dihydrochloride in 60 ml isopropanol for 1 hour. The mixture is stirred for 16 hours at ambient temperature and for 4 hours at 60° C. The solvent is removed under reduced pressure. The crude product is triturated with acetone and suction filtered. Yield: 0.40 g (73% of theory), R$_f$ value: 0.62 (silica gel; methylene chloride/methanol/conc. ammonia = 2:1:0.25)

Mass spectrum: M+ = 415

The following compounds are obtained analogously to Example 7:

(1) 1-(4-amidinophenyl)-4-[N-[trans-4-(cyclohexyloxy-carbonyl)-cyclohexyl]-aminocarbonyl]-piperazine-dihydrochloride The reaction is carried out in a mixture of solvents consisting of cyclohexane/methylene chloride. After hydrogen chloride has been passed through, the methylene chloride is distilled off and the suspension is stirred for 4 hours at 90° C. The product is precipitated with ether. R$_f$ value: 0.61 (silica gel; methylene chloride/methanol/conc. ammonia = 2:1:0.25)

Mass spectrum: (M+H)+ = 456

(2) 1-(4-amidinophenyl)-4-[N-[trans-4-(cyclohexyloxy-carbonyl)-cyclohexyl]-N-methyl-aminocarbonyl]-piperazine-dihydrochloride The reaction is carried out in a solvent mixture of cyclohexanol/methylene chloride. The mixture is stirred for 16 hours at 50° C. R$_f$ value: 0.58 (silica gel; methylene chloride/methanol/conc. ammonia = 2:1:0.25)

Mass spectrum: (M+H)+ = 470

(3) 1-(4-amidinophenyl)-4-[N-[trans-4-(isopropoxy-carbonyl)-cyclohexyl]-N-methyl-aminocarbonyl]-piperazine-dihydrochloride The methyl ester is used instead of the free acid. It is stirred for 24 hours at 50° C. Then, glacial acetic acid is added and the mixture is stirred for a further 24 hours at 50° C. R$_f$ value: 0.21 (Reversed Phase Plate RP18; methanol/5% saline solution = 6:4)

Mass spectrum: M+ = 429

(4) 1-(4-amidinophenyl)-4-[N-[trans-4-(ethoxycarbonyl)-cyclohexyl]-N-methyl-aminocarbonyl]-piperazine-dihydrochloride (5) 1-(4-amidinophenyl)-4-[N-[cis-4-(isopropoxy-carbonyl)-cyclohexyl]-N-methyl-aminocarbonyl]-piperazine-dihydrochloride R$_f$ value: 0.27 (Reversed Phase Plate RP18; methanol/5% saline solution = 6:4)

Mass spectrum: M+ = 429

(6) 1-(5-amidinopyrid-2-yl)-4-[N-[trans-4-(isopropoxy-carbonyl)-cyclohexyl]-N-methyl-aminocarbonyl]-piperazine-dihydrochloride R$_f$ value: 0.67 (silica gel; methylene chloride/methanol/conc. ammonia = 2:1:0.25)

Mass spectrum: (M+H)+ = 431

(7) 4-(4-amidinophenyl)-1-[N-[trans-4-(isopropoxycarbonyl)-cyclohexyl]-aminocarbonyl]-piperidine-hydrochloride The reaction is carried out in isopropanol/ethereal hydrochloric acid (5:2). It is stirred for 24 hours at ambient temperature. The crude product is triturated with ether. R$_f$ value: 0.27 (silica gel; methylene chloride/methanol/conc. ammonia = 4:1:0.25)

Mass spectrum: M+ = 414

(8) 4-(4-amidinophenyl)-1-[N-[trans-4-(cyclohexyloxy-carbonyl)-cyclohexyl]-aminocarbonyl]-piperidine-hydrochloride The reaction is carried out in cyclohexanol/ethereal hydrochloric acid. It is stirred for 24 hours at ambient temperature. The crude product is triturated with ether. R$_f$ value: 0.25 (silica gel; methylene chloride/methanol/conc. ammonia = 4:1:0.25)

Mass spectrum: (M+H)+ = 455

(9) 4-(4-amidinophenyl)-1-[N-[trans-4-(isobutoxy-carbonyl)-cyclohexyl]-aminocarbonyl]-piperidine-hydrochloride The reaction is carried out in isobutanol/ethereal hydrochloric acid (5:2). The mixture is stirred for 4 hours at ambient temperature. The crude product is triturated with ether. R$_f$ value: 0.24 (silica gel; methylene chloride/methanol/conc. ammonia = 4:1:0.25)

Mass spectrum (M+H)+ = 429

(10) 4-(4-amidinophenyl)-1-[N-methyl-N-[trans-4-(isopropoxycarbonyl)-cyclohexyl]-aminocarbonyl]-piperidine-hydrochloride The reaction is carried out in isopropanol/ethereal hydrochloric acid (5:2). The crude product is chromatographed over silica gel. R$_f$ value: 0.32 (silica gel; methylene chloride/methanol/conc. ammonia = 4:1:0.25)

Mass spectrum (M+H)+ = 429

(11) 1-(4-amidinophenyl)-4-[4-(ethoxycarbonylmethyl)-piperidinocarbonyl]-piperidine-dihydrochloride

(12) 1-(4-amidinophenyl)-4-[4-(isopropyloxycarbonyl-methyl)-piperidinocarbonyl]-piperidine-dihydrochloride Melting point: 208°-210° C. (decomp.)

(13) 1-(4-amidinophenyl)-4-[4-(cyclopentyloxycarbonyl-methyl)-piperidinocarbonyl]-piperidine-dihydrochloride

(14) 1-(4-amidinophenyl)-4-[4-(cyclohexyloxycarbonyl-methyl)-piperidinocarbonyl]-piperidine-dihydrochloride Melting point: 250°-252° C. (decomp.)

(15) 1-(4-amidinophenyl)-4-[4-[(3-n-pentyloxy)-carbonyl-methyl]-piperidinocarbonyl]-piperidine-dihydrochloride

(16) 1-(4-amidinophenyl)-4-[4-(isobutyloxy)-carbonyl-methyl]-piperidinocarbonyl]-piperidine-dihydrochloride

(17) 1-(4-amidinophenyl)-4-[N-[3-(isopropyloxycarbonyl)-propyl]-N-methyl-aminocarbonyl]-piperidine-dihydrochloride

(18) 1-(4-amidinophenyl)-4-[4-(isopropoxycarbonylmethylidene)-piperidinocarbonyl]-piperidine-dihydrochloride

(19) 1-(4-amidinophenyl)-4-[N-[2-(benzyloxycarbonyl)-ethyl]-aminocarbonylmethyl]-piperidine-dihydrochloride

(20) 1-(4-amidinophenyl)-4-[N-[trans-4-(isopropyloxycarbonyl)-cyclohexyl]-aminocarbonyl]-piperidine-dihydrochloride Melting point: 272°–275° C. (decomp.)

(21) 1-(4-amidinophenyl)-4-[N-[trans-4-(isobutyloxy carbonyl)-cyclohexyl]-aminocarbonyl]-piperidine-dihydrochloride Melting point: 282°–284° C. (decomp.)

(22) 1-(4-amidinophenyl)-4-[N-[trans-4-(cyclohexyloxy-carbonyl)-cyclohexyl]-aminocarbonyl]-piperidine-dihydrochloride Melting point: 275°–279° C. (decomp.)

(23) 1-(4-amidinophenyl)-4-[4-(isopropyloxycarbonyl-methyl)-piperidinocarbonyl]-piperazine-dihydrochloride

(24) 1-(4-amidinophenyl)-4-[4-(isobutyloxycarbonylmethyl)-piperidinocarbonyl]-piperazine-dihydrochloride

(25) 1-(4-amidinophenyl)-4-[ 4-(cyclohexyloxycarbonyl-methyl)-piperidinocarbonyl]-piperazine-dihydrochloride

(26) 1-(4-amidinophenyl)-4-[N-[2-(isopropyloxycarbonyl)-ethyl]-aminocarbonylmethyl]-piperazine-trihydrochloride

(27) 1-(4-amidinophenyl)-4-[N-[2-(3-n-pentyloxy-carbonyl)-ethyl]-aminocarbonylmethyl]-piperazine-trihydrochloride

(28) 1-(4-amidinophenyl)-4-[N-[2-(cyclohexyloxycarbonyl)-ethyl]-aminocarbonylmethyl]-piperazine-trihydrochloride

(29) 1-(4-aminomethylphenyl)-4-[N-[trans-4-(isopropoxycarbonyl)-cyclohexyl]-aminocarbonyl]-piperazine-dihydrochloride

(30) 1-(4-amidinophenyl)-4-[N-[trans-4-(cyclopentyloxycarbonyl)-cyclohexyl]-N-methyl-aminocarbonyl]-piperazine-dihydrochloride

(31) 1-(4-aminomethylphenyl)-4-[N-[trans-4-(2-butyloxycarbonyl)-cyclohexyl]-N-methyl-aminocarbonyl]-piperazine-dihydrochloride

(32) 1-(4-amidinophenyl)-4-[N-benzyl-N-[trans-4-(isopropoxycarbonyl)-cyclohexyl]-aminocarbonyl]-piperazine-dihydrochloride

(33) 1-(4-amidinophenyl)-4-[N-benzyl-N-[trans-4-(cyclopentylmethoxycarbonyl)-cyclohexyl]-amino-carbonyl]-piperazine-dihydrochloride

(34) 1-(5-amidinopyrid-2-yl)-4-[N-[trans-4-(pyridyl-methoxycarbonyl)-cyclohexyl]-aminocarbonyl]-piperazine-dihydrochloride

(35) 1-(5-amidinopyrid-2-yl)-4-[N-[trans-4-(isobutoxy-carbonyl)-cyclohexyl]-aminocarbonyl]-piperazine-dihydrochloride

(36) 1-(5-aminomethylpyrid-2-yl)-4-[N-[trans-4-(cyclopentyloxycarbonyl)-cyclohexyl]-aminocarbonyl]-piperazine-dihydrochloride

(37) 1-(5-amidinopyrid-2-yl)-4-[N-[trans-4-(isopropoxycarbonyl)-cyclohexyl]-aminocarbonyl]-piperidine-dihydrochloride

(38) 1-(5-amidinopyrid-2-yl)-4-[N-[trans-4-(cyclohexyl-methoxycarbonyl)-cyclohexyl]-aminocarbonyl]-piperidine-dihydrochloride

(39) 4-(4-amidinophenyl)-1-[N-[trans-4-(ethoxycarbonyl)-cyclohexyl]-aminocarbonyl]-piperidine-hydrochloride

(40) 4-(4-amidinophenyl)-1-[N-benzyl-N-[trans-4-(n-butyloxycarbonyl)-cyclohexyl]-aminocarbonyl]-piperidine-hydrochloride

(41) 1-(4-amidinophenyl)-4-[N-methyl-N-[trans-4-(isopropoxycarbonyl)-cyclohexyl]-aminomethyl]-piperidine-trihydrochloride

(42) 1-(4-amidinophenyl)-4-[N-[trans-4-(cyclohexyloxycarbonyl)-cyclohexyl]-N-methyl-aminomethyl]-piperidine-trihydrochloride

(43) 1-(4-amidinophenyl)-4-[4-[(isopropoxycarbonyl)-methyl]-piperidinomethyl]-piperidine-trihydrochloride

(44) 1-(4-amidinophenyl)-4-[4-[(cyclohexyloxycarbonyl)-methyl]-piperidinomethyl]-piperidine-trihydrochloride

EXAMPLE 8

1-(4-Amidinophenyl)-4-[N-[trans-4-(ethoxycarbonyl)-cyclohexyl]-aminocarbonyl]-piperazine-dihydrochloride A suspension of 0.5 g of 1-(4-amidinophenyl)-4-[N-(trans 4-carboxycyclohexyl)-aminocarbonyl]-piperazine-dihydrochloride in 10 ml of thionylchloride is stirred for 16 hours at ambient temperature. Excess thionylchloride is removed under reduced pressure. The residue remaining is dissolved in 20 ml of methylenechloride and 20 ml of ethanol. The mixture is stirred for 2 hours at ambient temperature and for 4 hours at 50° C. The solvent is removed at reduced pressure and the residue remaining is triturated with acetone and suction filtered. Yield: 0.43 g (84% of theory), $R_f$ value: 0.61 (silica gel; methylene chloride/methanol/conc. ammonia=2:1:0.25)

Mass spectrum: $(M+H)^+ = 402$

The following compounds are obtained analogously to Example 8:

(1) 1-(4-amidinophenyl)-4-[4-[(2-(R)-butyloxy)-carbonyl-methyl]-piperidinocarbonyl]-piperidine-dihydrochloride (2) 1-(4-amidinophenyl)-4-[4-[(2-(S)-butyloxy)-carbonyl-methyl]-piperidinocarbonyl]-piperidine-dihydrochloride (3) 4-(4-amidinophenyl)-1-[4-[(2-(R)-butyloxy)-carbonyl-methyl]-piperidinocarbonyl]-piperidine-hydrochloride (4) 4-(4-amidinophenyl)-1-[4-[(2-(S) -butyloxy)-carbonyl-methyl]-piperidinocarbonyl]-piperidine-hydrochloride (5) 1-(4-amidinophenyl)-4-[4-[( 2-morpholinoethyloxy)-carbonylmethyl]-piperidinocarbonyl-piperidine-trihydrochloride (6) 1-(4-amidinophenyl)-4-[4-[[2-(2-oxo-pyrrolidino)-ethyl]-oxocarbonylmethyl]-piperidinocarbonyl]-piperidine-dihydrochloride (7) 1-(4-amidinophenyl)-4-[4-[(dimethylaminocarbonyl)-methoxycarbonylmethyl]-piperidinocarbonyl]-piperidine-dihydrochloride (8) 1-(4-amidinophenyl)-4-[4-(exo-norborn-2-yloxycarbonylmethyl)-piperidinocarbonyl]-piperidine-dihydrochloride (9) 1-(4-amidinophenyl)-4-[4-[trans-4-[(−)-menthyl-oxycarbonyl]-cyclohexyl]-aminocarbonyl]-piperidine-dihydrochloride

(10) 1-(4-amidinophenyl)-4-[4-[(2-(R)-butyloxy)-carbonylmethyl]-piperidinocarbonyl]-piperazine-dihydrochloride

(11) 1-(4-amidinophenyl)-4-[4-[(2-(S)-butyloxy)-carbonylmethyl]-piperidinocarbonyl]-piperazine-dihydrochloride

(12) 1-(4-amidinophenyl)-4-[N-[trans-4-(benzyloxycarbonyl)-cyclohexyl]-aminocarbonyl]-piperazine-dihydrochloride

(13) 1-(4-amidinophenyl)-4-[N-[trans-4-(cyclohexylmethoxycarbonyl)-cyclohexyl]-aminocarbonyl]-piperazine-dihydrochloride

(14) 1-(4-amidinophenyl)-4-[N-[trans-4-(isobutoxycarbonyl)-cyclohexyl]-aminocarbonyl]-piperazine-dihydrochloride

(15) 1-(4-amidinophenyl)-4-[N-[trans-4-(2-morpholino-ethoxycarbonyl)-cyclohexyl]-aminocarbonyl]-piperazin-dihydrochloride

(16) 1-(4-amidinophenyl)-4-[N-[trans-4-(endo-norborn-2-yloxycarbonyl)-cyclohexyl]-aminocarbonyl]-piperazine-dihydrochloride

EXAMPLE 9

1-(4-Amidinophenyl)-4-[N-[trans-4-[(morpholinocarbonyl)-me thoxycarbonyl]-cyclohexyl]-aminocarbonyl]-piperazine-hydrochloride A solution of 300 mg of 1-[4-(N-benzyloxycarbonyl-amidino)-phenyl]-4-[N-[trans-4-[(morpholinocarbonyl)-methoxycarbonyl]-cyclohexyl]-aminocarbonyl]-piperazine in 20 ml dimethylformamide is hydrogenated for 2 hours in the presence of 0.3 g of a catalyst consisting of 10% palladium on activated charcoal under an excess hydrogen pressure of 5 bar. Ethereal hydrochloric acid is added and the mixture is filtered. The filtrate is evaporated down under reduced pressure and the residue remaining is triturated with ether/acetone, acetone and acetone/methylene chloride and suction filtered. Yield: 210 mg (83% of theory), $R_f$ value: 0.27 (silica gel; methylene chloride/methanol/conc. ammonia=4:1:0.25)

Mass spectrum: $(M+H)^+ = 501$

The following compounds are obtained analgously to Example 9:

(1) 1-(4-amidinophenyl)-4-[N-[trans-4-[(dimethylamino-carbonyl)-methoxycarbonyl]-cyclohexyl]-aminocarbonyl]-piperazine-hydrochloride The hydrogenation is carried out in a solvent mixture of acetone/dimethylformamide. The catalyst is filtered off and the crude product is precipitated with ether. Then, the hydrochloride is prepared using ethereal hydrochloric acid.

$R_f$ value: 0.15 (silica gel; methylene chloride/methanol/conc. ammonia=4:1:0.25)

Mass spectrum: $(M+H)^+ = 459$ (2) 1-(4-amidinophenyl)-4-[N-[trans-4-[(piperidinocarbonyl)-methoxycarbonyl]-cyclohexyl]-aminocarbonyl]-piperazine-hydrochloride (3) 4-(4-amidinophenyl)-1-[N-[trans-4-[(dimethylamino-carbonyl)-methoxycarbonyl]-cyclohexyl]-aminocarbonyl]-piperidine-hydrochloride (4) 4-(4-amidinophenyl)-1-[N-[trans-4-[(piperidinocarbonyl)-methoxycarbonyl]-cyclohexyl]-aminocarbonyl]-piperidine-hydrochloride (5) 4-(4-amidinophenyl)-1-[N-[trans-4-[(morpholinocarbonyl)-methoxycarbonyl]-cyclohexyl]-aminocarbonyl]-piperidine-hydrochloride

EXAMPLE 10

1-[4-(N-Benzyloxycarbonylamidino)-phenyl]-4-[4-[pivaloyloxymethyloxycarbonylmethyl]-piperidinocarbonyl]-piperidine A suspension of 1 equivalent of 1-[4-(N-benzyloxycarbonylamidino)-phenyl]-4-[4-(carboxymethyl)-piperidinocarbonyl]-piperidine is stirred for 2 days with 2 equivalents each of chloromethyl pivalate, potassium iodide, potassium bicarbonate and potassium carbonate in dimethylformamide at ambient temperature for 2 days. After pouring into water, extraction with ethyl acetate and evaporation down of the ethyl acetate extract, the desired product is obtained which is then chromotagraphed over silica gel. The following compounds are obtained analogously to Example 10:

(1) 1-[4-(N-benzyloxycarbonylamidino)-phenyl]-4-[4-[[1-(ethoxycarbonyloxy)-ethoxycarbonyl]-methyl]-piperidinocarbonyl]-piperidine Using 1-(ethoxycarbonyloxy)-ethylchloride (2) 1-[4-(N-benzyloxycarbonylamidino)-phenyl]-4-[trans-4-(pivaloyloxymethyloxycarbonyl)-cyclohexylamino-carbonyl]-piperazine Mass spectrum: $(M+H)^+ = 622$ (3) 1-[4-(N-benzyloxycarbonylamidino)-phenyl]-4-[[trans-4-[1-(ethoxycarbonyloxy)-ethoxycarbonyl]-cyclo-hexyl-amino]-carbonyl]-piperazine Using 1-(Ethoxycarbonyloxy)-ethylchloride Mass spectrum: $(M+H)^+ = 624$

EXAMPLE 11

1-(4-Amidinophenyl)-4-[4-[(pivaloyloxymethyl)-oxycarbonylmethyl]-piperidinocarbonyl]-piperidine-hydrochloride 1-[4-(N-Benzyloxycarbonylamidino)-phenyl]-4-[4-[(pivaloyloxymethyl)-oxycarbonylmethyl]-piperidinocarbonyl]-piperidine is hydrogenated in dimethylformamide/0.5N hydrochloric acid (10:1) using 10% palladium on charcoal under a pressure of 5 bar. After the removal of the catalyst, a pH of 3 is established and the solvent is removed under reduced pressure. The residue remaining is suspended in acetone and suction filtered.

The following compounds are obtained analogously to Example 11:

(1) 1-(4-amidinophenyl)-[4-[1-(ethoxycarbonyloxy)-ethoxycarbonylmethyl]-piperidinocarbonyl]-piperidine-hydrochloride (2) 1-(4-amidinophenyl)-4-[trans-4-(pivaloyloxymethyl-oxycarbonyl)-cyclohexylaminocarbonyl]-piperazine-hydrochloride Mass spectrum: $(M+H)^+ = 488$ (3) 1-(4-amidinophenyl)-4-[[trans-4-[1-(ethoxycarbonyl-oxy)-ethoxycarbonyl]-cyclohexylamino]-carbonyl]-piperazine-hydrochloride Mass spectrum: $(M+H)^+ = 490$

EXAMPLE 12

Dry ampoule containing 2.5 mg of active substance per 1 ml

Composition:

| | |
|---|---|
| Active substance | 2.5 mg |
| Mannitol | 50.0 mg |
| Water for injections ad | 1.0 ml |

Preparation:

The active substance and mannitol are dissolved in water. After transferring the solution to the ampoule, it is freeze-dried. At the point of use, the solution is made up with water for injections.

EXAMPLE 13

Dry ampoule containing 35 mg of active substance per 2 ml
Composition:

| Active substance | 35.0 mg |
|---|---|
| Mannitol | 100.0 mg |
| Water for injections ad | 2.0 ml |

Preparation:
The active substance and mannitol are dissolved in water. After transferring the solution to the ampoule, it is freeze-dried.

At the point of use, the solution is made up with water for injections.

EXAMPLE 14

Tablet containing 50 mg of active substance
Composition:

| (1) Active substance | 50.0 mg |
|---|---|
| (2) Lactose | 98.0 mg |
| (3) Corn starch | 50.0 mg |
| (4) Polyvinylpyrrolidone | 15.0 mg |
| (5) Magnesium stearate | 2.0 mg |
| | 215.0 mg |

Preparation:
(1), (2) and (3) are mixed together and granulated with an aqueous solution of (4). (5) is added to the dried granules. From this mixture, compressed tablets are produced, biplanar, facetted on both sides and notched on one side. Diameter of tablets: 9 mm.

EXAMPLE 15

Tablet containing 350 mg of active substance
Composition:

| (1) Active substance | 350.0 mg |
|---|---|
| (2) Lactose | 136.0 mg |
| (3) Corn starch | 80.0 mg |
| (4) Polyvinylpyrrolidone | 30.0 mg |
| (5) Magnesium stearate | 4.0 mg |
| | 600.0 mg |

Preparation:
(1), (2) and (3) are mixed together and granulated with an aqueous solution of (4). (5) is added to the dried granules. From this mixture, compressed tablets are produced, biplanar, facetted on both sides and notched on one side. Diameter of tablets: 12 mm.

EXAMPLE 16

Capsules containing 50 mg of active substance
Composition:

| (1) Active substance | 50.0 mg |
|---|---|
| (2) Dried corn starch | 58.0 mg |
| (3) Powdered lactose | 50.0 mg |
| (4) Magnesium stearate | 2.0 mg |
| | 160.0 mg |

Preparation:
(1) is triturated with (3). This triturate is added to the mixture of (2) and (4), with thorough mixing.

This powdered mixture is packed into size 3 hard gelatin oblong capsules in a capsule filling machine.

EXAMPLE 17

Capsules containing 350 mg of active substance
Composition:

| (1) Active substance | 350.0 mg |
|---|---|
| (2) Dried corn starch | 46.0 mg |
| (3) Powdered lactose | 30.0 mg |
| (4) Magnesium stearate | 4.0 mg |
| | 430.0 mg |

Preparation:
(1) is triturated with (3). This triturate is added to the mixture of (2) and (4), with thorough mixing.

This powdered mixture is packed into size 0 hard gelatin oblong capsules in a capsule filling machine.

What is claimed is:
1. Carboxylic acid derivatives of the formula

$$A-B-C-D-E-F-G \qquad (I)$$

wherein
A denotes a $C_{1-2}$-aminoalkyl group or an amidino group, in which at a nitrogen atom in the above-mentioned groups, a hydrogen atom may be replaced by an alkoxycarbonyl group having a total of 2 or 3 carbon atoms or by a benzyloxycarbonyl, allyloxycarbonyl or $R_1-CO-O-(R_2C-H)-O-CO-$ group, wherein
  $R_1$ denotes a $C_{1-2}$-alkyl group and
  $R_2$ denotes a hydrogen atom or a $C_{1-2}$-alkyl group;
B denotes a pyridinylene group optionally substituted in the carbon skeleton by a fluorine, chlorine or bromine atom or by a methyl group;
C denotes a piperazinylene group;
D denotes a carbonyl group;
E denotes an $-NR_4-X-$ group, wherein
  X represents a 1,4-cyclohexylene group, and
  $R_4$ denotes a hydrogen atom, a $C_{1-6}$-alkyl group or a phenylalkyl group having 1 to 4 carbon atoms in the alkyl moiety;
F denotes a bond; and
G denotes a carbonyl group substituted by an $R_5O-$ group,
wherein
  $R_5$ denotes a hydrogen atom, a $C_{1-6}$-alkyl group, a phenylmethyl group, a cycloalkyl or cycloalkylmethyl group each having 5 or 6 carbon atoms in the cycloalkyl moiety, or a menthyl or norbornyl group;
or G denotes an $R_6CO-O-CHR_2-O-CO-$ group, wherein
  $R_2$ is as hereinbefore defined, and
  $R_6$ denotes a $C_{1-4}$-alkyl group or a methoxy or ethoxy group;
the tautomers thereof, the stereoisomers thereof including the mixtures thereof, and the addition salts thereof.

2. The carboxylic acid derivatives as recited in claim 1, wherein A denotes an aminomethyl or amidino group, in which at a nitrogen atom in the amidino group, a hydrogen atom may be replaced by a methoxycarbonyl, ethoxycarbonyl or benzyloxycarbonyl group;

B denotes a pyridinylene group;
C denotes a piperazinylene group;
D denotes a carbonyl group;
E denotes an —NR$_4$—X— group, wherein
X represents a 1,4-cyclohexylene group, and
R$_4$ denotes a hydrogen atom, a C$_{1-5}$-alkyl group or a phenylalkyl group having 1 to 3 carbon atoms in the alkyl moiety;
F denotes a bond; and
G denotes a carbonyl group substituted by an R$_5$—O group,
wherein
R$_5$ represents hydrogen atom, a C$_{1-5}$-alkyl group or C$_{5-6}$-cycloalkyl group; the tautomers thereof, the stereoisomers thereof including mixtures thereof, and the addition salts thereof.

3. The carboxylic acid derivatives as recited in claim 1, wherein:

A and B together denote a 5-amidino-pyrid-2-yl group;
C denotes a piperazinylene group;
D denotes a carbonyl group;
E denotes an —NR$_4$—X— group, wherein
X represents 1,4-cyclohexylene group, and
R$_4$ denotes a hydrogen atom, a straight-chained C$_{1-5}$-alkyl group or a benzyl, 2-phenylethyl or 3-phenylpropyl group;
F denotes a bond; and
G denotes a carbonyl group substituted by an R$_5$O— group,
wherein
R$_5$ denotes a hydrogen atom, a C$_1$-C$_4$-alkyl group or a cyclohexyl group; the stereoisomers thereof including mixtures thereof and the addition slats thereof.

4. 1-(5-amidinopyrid-2-yl)-4-[N-(trans-4-carboxycyclohexyl)-aminoocarbonyl]-piperazine, the esters thereof with cyclohexanol or with a C$_{1-4}$-alkanol, the stereoisomers thereof including mixtures thereof, and the addition salts thereof.

5. 1-(5-amidinopyrid-2-yl)-4-[N-(trans-4-carboxycyclohexyl)-N-methyl-aminocarbonyl]-piperazine, the esters thereof with cyclohexanol or with a C$_{1-4}$-alkanol, the stereoisomers thereof including mixtures thereof, and the addition salts thereof.

6. 1-(5-aminomethylpyrid-2-yl)-4-[N-(trans-4-carboxycyclohexyl)-aminocarbonyl]-piperazine, the esters thereof with cyclohexanol or with a C$_{1-4}$-alkanol, the stereoisomers thereof including mixtures thereof, and the addition salts thereof.

* * * * *